(12) United States Patent
Horsman et al.

(10) Patent No.: US 6,783,673 B2
(45) Date of Patent: Aug. 31, 2004

(54) COMPOSITE CHROMATOGRAPHY COLUMN

(75) Inventors: Jeffrey A. Horsman, Charlottesville, VA (US); Peter C. Van Davelaar, Charlottesville, VA (US)

(73) Assignee: Biotage, Inc., Charlottesville, VA (US)

( * ) Notice: Subject to any disclaimer, the term of this patent is extended or adjusted under 35 U.S.C. 154(b) by 0 days.

(21) Appl. No.: 10/226,530

(22) Filed: Aug. 23, 2002

(65) Prior Publication Data

US 2004/0035774 A1 Feb. 26, 2004

(51) Int. Cl.⁷ .............................................. B01D 15/08
(52) U.S. Cl. ...................... 210/198.2; 210/656; 96/105
(58) Field of Search ................................ 210/635, 656, 210/198.2, 232, 238, 282, 541; 96/101, 105, 104, 106

(56) References Cited

U.S. PATENT DOCUMENTS

| | | |
|---|---|---|
| 1,101,084 A | 6/1914 | McCarty |
| 1,736,610 A | 11/1929 | Loffler |
| 2,401,231 A | 5/1946 | Crawford |
| 2,647,847 A | 8/1953 | Black et al. |
| 2,998,036 A | 8/1961 | Strashein et al. |
| 3,266,554 A | 8/1966 | Brownrigg |
| 3,300,849 A | 1/1967 | Wisemam |
| 3,398,512 A | 8/1968 | Perkins, Jr. et al. |
| 3,440,864 A | 4/1969 | Blume |
| 3,483,986 A | 12/1969 | Wright |
| 3,511,377 A | 5/1970 | Hrdina |
| 3,574,352 A | 4/1971 | Rackoff et al. |
| 3,615,235 A | 10/1971 | Hrdina |
| 3,682,315 A | 8/1972 | Haller |
| 3,692,669 A | 9/1972 | Bauman |
| 3,731,367 A | 5/1973 | Laussermair et al. |
| 3,763,879 A | 10/1973 | Jaworck |
| 3,900,939 A | 8/1975 | Greacen |
| 3,902,849 A | 9/1975 | Barak et al. |
| 3,912,516 A | 10/1975 | Recchia et al. |

(List continued on next page.)

OTHER PUBLICATIONS

Chemical Week; Oct. 31, 2001; Hunter, David.*
International Search Report, Feb. 19, 2004, PCT.
POROS 50 EP and OH Perfusion Chromatography, "Operating Instructions", pp. 1–2.
3M Emphaze—Biosupport Medium, "Introducton to CM Emphaze Biosupport Medium,"pp. 1–3 1992.
EM Separations Technology, "Tentacle Ion Exchange Chromatography Handbook," pp. 1 and 4.
EM Separations Technology, Superformance Pilot and Production Glass Columns, "Chromatography Columns" pp. 68–71, 1995.

(List continued on next page.)

Primary Examiner—Ernest G. Therkorn
(74) Attorney, Agent, or Firm—Fish & Richardson P.C.

(57) ABSTRACT

Apparatus for chromatography, featuring a composite chromatography column including a tubular member having an inlet end and an outlet end, where the tubular member includes an innermost first layer comprised of a first material and a second layer comprised of a second material. The chromatography apparatus can also include a first intermediate layer formed from a third material, where at least a portion of the first intermediate layer is disposed between the innermost first layer and the second layer. A second intermediate layer formed from a fourth material, can further be included in the chromatography apparatus, where at least a portion of the second intermediate layer is disposed between the innermost first layer and the second layer. A portion of the second intermediate layer can be disposed between the second layer and the first intermediate layer.

21 Claims, 21 Drawing Sheets

U.S. PATENT DOCUMENTS

| | | |
|---|---|---|
| 3,935,884 A | 2/1976 | Hazelton |
| 3,951,657 A | 4/1976 | Recchia et al. |
| 3,966,609 A | 6/1976 | Godbille et al. |
| 3,978,575 A | 9/1976 | Beyer et al. |
| 4,093,550 A | 6/1978 | Stahl et al. |
| 4,167,351 A | 9/1979 | Bindin |
| 4,186,606 A | 2/1980 | Tarumi et al. |
| 4,187,177 A | 2/1980 | Stahl |
| 4,198,081 A | 4/1980 | Harrison et al. |
| 4,245,494 A | 1/1981 | Legendre et al. |
| 4,250,035 A | 2/1981 | McDonald et al. |
| 4,280,905 A | 7/1981 | Gunkel et al. |
| 4,283,280 A | 8/1981 | Brownlee |
| 4,293,942 A | 10/1981 | Baumgartner |
| 4,314,396 A | 2/1982 | Nunlist et al. |
| 4,332,073 A | 6/1982 | Yoshida et al. |
| 4,333,223 A | 6/1982 | Germann |
| 4,354,932 A | 10/1982 | McNeil |
| 4,361,482 A | 11/1982 | Teetz et al. |
| 4,375,743 A | 3/1983 | Sullivan |
| 4,377,335 A | 3/1983 | Fannon et al. |
| 4,377,894 A | 3/1983 | Yoshida |
| 4,384,957 A | 5/1983 | Crowder, III et al. |
| 4,451,365 A | 5/1984 | Sättler et al. |
| 4,457,846 A | 7/1984 | Munk |
| 4,483,374 A | 11/1984 | Siemion |
| 4,549,584 A | 10/1985 | Morin et al. |
| 4,551,249 A | 11/1985 | Shackelford et al. |
| 4,557,830 A | 12/1985 | Onitsuka et al. |
| 4,565,632 A | 1/1986 | Hatch et al. |
| 4,582,608 A | 4/1986 | Ritacco |
| 4,597,866 A | 7/1986 | Couillard |
| 4,627,918 A | 12/1986 | Saxena |
| 4,636,315 A | 1/1987 | Allen, Jr. |
| 4,636,316 A | 1/1987 | Harris et al. |
| 4,655,917 A | 4/1987 | Shackelford et al. |
| 4,670,141 A | 6/1987 | Shackelford et al. |
| 4,692,243 A | 9/1987 | Porsch et al. |
| 4,719,011 A | 1/1988 | Shalon et al. |
| 4,732,632 A | 3/1988 | Pieslak et al. |
| 4,732,687 A | 3/1988 | Muller et al. |
| 4,737,284 A | 4/1988 | Hauke et al. |
| 4,737,292 A | 4/1988 | Ritacco et al. |
| 4,755,293 A | 7/1988 | Sakamoto et al. |
| 4,769,141 A | 9/1988 | Couillard |
| 4,806,238 A | 2/1989 | Sättler et al. |
| 4,861,473 A | 8/1989 | Shackelford et al. |
| 4,865,728 A | 9/1989 | Larsson |
| 4,865,729 A | 9/1989 | Saxena et al. |
| 4,876,005 A | 10/1989 | America |
| 4,882,047 A | 11/1989 | Shalon |
| 4,890,753 A | 1/1990 | Duryee et al. |
| 4,891,133 A | 1/1990 | Colvin, Jr. |
| 4,927,531 A | 5/1990 | Sakamoto et al. |
| 4,968,421 A | 11/1990 | Spacek et al. |
| 4,976,307 A | 12/1990 | Hall et al. |
| 4,997,465 A | 3/1991 | Stanford |
| 5,021,162 A | 6/1991 | Sakamoto et al. |
| 5,069,069 A | 12/1991 | Miyagishi et al. |
| 5,089,125 A | 2/1992 | Hart et al. |
| 5,137,628 A | 8/1992 | Hart et al. |
| 5,141,635 A | 8/1992 | LePlang |
| 5,167,809 A | 12/1992 | Mann et al. |
| 5,167,810 A | 12/1992 | Vassarotti et al. |
| 5,169,522 A | 12/1992 | Shalon et al. |
| 5,192,433 A | 3/1993 | Shalon |
| 5,194,225 A | 3/1993 | Müller et al. |
| 5,199,171 A | 4/1993 | Umezawa et al. |
| 5,227,059 A | 7/1993 | Shepherd |
| 5,234,599 A | 8/1993 | Cortes et al. |
| 5,238,556 A | 8/1993 | Shirkhan |
| 5,282,973 A | 2/1994 | Mann |
| 5,324,426 A | 6/1994 | Joseph et al. |
| 5,324,427 A | 6/1994 | Traveset-Masanes et al. |
| 5,338,448 A | 8/1994 | Gjerde |
| 5,366,621 A | 11/1994 | Bidell |
| 5,378,361 A | 1/1995 | Baeckström |
| 5,423,982 A | 6/1995 | Jungbauer |
| 5,462,660 A | 10/1995 | Singleton |
| 5,482,628 A | 1/1996 | Schick |
| 5,601,708 A | 2/1997 | Leavesley |
| 5,614,089 A | 3/1997 | Allington |
| 5,645,715 A | 7/1997 | Coombs |
| 5,651,885 A * | 7/1997 | Schick ............... 210/198.2 |
| 5,651,886 A | 7/1997 | Hoffman |
| 5,671,928 A | 9/1997 | Lanyi et al. |
| 5,693,223 A | 12/1997 | Yamada et al. |
| 5,714,074 A | 2/1998 | Karlsson et al. |
| 5,714,677 A | 2/1998 | Parsy et al. |
| 5,736,036 A * | 4/1998 | Upchurch et al. ....... 210/198.2 |
| 5,767,444 A | 6/1998 | Heimlicher |
| 5,820,762 A | 10/1998 | Bamer et al. |
| 5,906,932 A | 5/1999 | Kuriyama et al. |
| 6,001,253 A | 12/1999 | Conroy et al. |
| 6,019,897 A | 2/2000 | Horsman |
| 6,029,498 A | 2/2000 | Walters et al. |
| 6,051,189 A | 4/2000 | Wick et al. |
| 6,060,278 A | 5/2000 | Liu et al. |
| 6,074,556 A | 6/2000 | Van Davelaar |
| 6,086,766 A | 7/2000 | Yasui |
| 6,090,279 A | 7/2000 | Davis et al. |
| 6,103,111 A | 8/2000 | Kakamu et al. |
| 6,117,329 A | 9/2000 | Hargro |
| 6,132,605 A | 10/2000 | Leavesley et al. |
| 6,139,732 A | 10/2000 | Pelletier |
| 6,139,733 A * | 10/2000 | Hargro et al. ........... 210/198.2 |
| 6,162,362 A | 12/2000 | Ma et al. |
| 6,171,486 B1 | 1/2001 | Green et al. |
| 6,188,813 B1 | 2/2001 | Dourdeville et al. |
| 6,245,928 B1 | 6/2001 | Arghavani et al. |
| 6,277,283 B1 | 8/2001 | Davis et al. |
| 6,294,087 B1 | 9/2001 | Hargro et al. |
| 6,306,546 B1 | 10/2001 | LaFleur et al. |
| 6,387,256 B1 | 5/2002 | Tuvim |
| 6,398,953 B1 | 6/2002 | Hargro |
| 6,436,284 B1 | 8/2002 | Leavesley et al. |
| 6,444,122 B1 | 9/2002 | Van Davelaar |
| 6,494,500 B1 | 12/2002 | Todosiev et al. |
| 6,565,745 B2 | 5/2003 | Hodgin et al. |

OTHER PUBLICATIONS

BioSepra, "Hyper–Diffusion Chromatography", pp. 6, 7, 13, Apr. 1995.

Pharmacia Biotech—Process products '95, "High Purity in Industrial Chromatography".

Journal of Chromatography Library, Preparative Liquid Chromatography, vol. 38, pp. 79–80, 1987.

L.R. Snyder, J.J. Kirkland, Introduction to Modern Liquid Chromatography, Column Techniques, pp. 228–229, 250–251, 542–543 and 634–635, 1979.

Larry Miller, et al., "Solid injection, a new technique for application of insoluble samples in preparative liquid chromatography," Journal of Chromatography, vol. 484 (1989), pp. 259–265.

J. Kriz et al., "Solid sample introduction in preparative high–performance liquid chromatography: separation of diamantanols," Journal of Chromatography, vol. 248 (1982), pp. 303–307.

Patrick D. McDonald et al., "Strategies for successful preparative liquid chromatography," Chapter 1, section 1.6.2.2.6, "Sample Solubility," pp. 79–80, in Brian A. Bidlingmeyer, ed., Preparative Liquid Chromatography, (Amsterdam: Elsevier, 1987).

"Flash Sample Injection Module ™," Biotage, a Division of Dyax Corp., (1996).

Snyder, "Introduction to Modern Liquid Chromatography," (New York; John Wiley & Sons, 1979), pp. 228–229, 251, 543, and 635.

Pharmacia K 50 Column, p. 3, Pharmacia Laboratory Columns, XK Column System, pp. 424–426. (Cited by Examiner, no copy of).

* cited by examiner

COMPOSITE CHROMATOGRAPHY COLUMN

BACKGROUND OF THE INVENTION

The invention relates to columns used in liquid chromatography.

Liquid chromatography is a technique for separating the individual compounds that exist in a subject sample. In employing the technique, the subject sample is carried in a liquid, called a mobile phase. The mobile phase carrying the subject sample is caused to migrate through a media, sometimes called a stationary phase. Different compounds will have differing rates of migration through the media, which effects the separation of the components in the subject sample. Liquid chromatography is commonly performed with reusable columns or with disposable cartridges, both of which are usually cylindrical, in which the media bed is bounded axially by porous plates, or plates containing defined flow paths, through which the mobile phase will flow. (See U.S. Pat. No. 4,250,035 to McDonald et al.)

SUMMARY OF THE INVENTION

The present invention provides apparatus for chromatography. In general, in one aspect, the invention features a chromatography apparatus including a tubular member having an inlet end and an outlet end. The tubular member includes an innermost first layer comprised of a first material and a second layer comprised of a second material.

Embodiments of the invention may include one or more of the following. The chromatography apparatus can further include a first intermediate layer formed from a third material, where at least a portion of the first intermediate layer is disposed between the innermost first layer and the second layer. The first intermediate layer can be formed from an adhesive material. The chromatography apparatus can further include a second intermediate layer formed from a fourth material, where at least a portion of the second intermediate layer is disposed between the innermost first layer and the second layer. A portion of the second intermediate layer can be disposed between the second layer and the first intermediate layer.

The tubular member of the chromatography apparatus can include a plurality of layers, including at least the innermost first layer formed of the first material and a second layer formed of the second material. The second layer can be an intermediate layer and an outermost layer can be included, formed also of the first material. In one embodiment, the first material can encapsulate the second layer, thereby forming an outermost layer of the first material.

The outer surface of the second layer can have a cross-sectional shape having at least one flat side. For example, the outer surface can have a rectangular cross-sectional shape, or a square cross-sectional shape. In other embodiments, the outer surface can have a circular cross-sectional shape, a triangular cross-sectional shape, hexagonal cross-sectional shape or an octagonal cross-sectional shape.

The second layer can be formed from a deformable material and/or a rigid material. For example, the second layer can be formed from a polyolefin (e.g., polypropylene or polyethylene), stainless steel, aluminum, anodized aluminum, acetal, polycarbonate or glass. The innermost first layer can be formed from a chemically inert material. For example, the innermost first layer can be formed from a fluoropolymer, such as TEFLON, TEFZEL, EFEP or PTFE, and can be a lining, sleeve, or cladding. The innermost first layer may be impregnated in the second layer or may be formed by, coating, encapsulating, co-extrusion, anodizing, or bonding. Innermost first layers of TEFLON or like materials may be formed by TEFLON hardcoating or a similar technique. Forming an innermost first layer of TEFLON on an aluminum outer layer or intermediate layer surface through TEFLON hardcoating is an exemplary technique. The innermost first layer can also be formed from a deformable material and/or a rigid material. In one embodiment, the second layer can be formed from polypropylene and the innermost first layer formed from TEFLON. In another embodiment, the second layer can be formed from polyethylene and the innermost first layer formed from TEFLON.

In general, in another aspect, the invention features a chromatography column including a tubular member having an inlet and outlet end, first and second porous members disposed within the tubular member, and a chromatography or separation media disposed within the tubular member and bounded by the first and second porous members. The tubular member includes an innermost first layer formed from a chemically inert material and a second layer. The first porous member abuts the media and the first member is also in slidable contact with the inner layer of the tubular member, and is spaced sufficiently from the inlet end to define a module receiving region for receiving a sample module entirely within the tubular member.

Embodiments of the invention may include one or more of the following. The tubular member of the chromatography column can include a plurality of layers, including at least the innermost first layer (formed from the chemically inert material) and the second layer. The second layer can be an intermediate layer, and an outermost layer can be formed from the chemically inert material. In one embodiment the chemically inert material encapsulates the second layer, thereby forming both an innermost first layer and an outermost layer comprised of the chemically inert material.

The tubular member can further include a sealing region between the inlet end and the module receiving region. The sealing region is sufficiently long to receive a sealing head for making a seal with the innermost first surface of the tubular member. The tubular member can include a chamfered region near the inlet end.

The second layer of the chromatography column can be formed from polypropylene, polyethylene, stainless steel, aluminum, anodized aluminum, acetal, polycarbonate or glass. The innermost first layer of the chromatography column can be formed from a fluoropolymer, such as TEFLON, TEFZEL, EFEP or PTFE. In one embodiment, the second layer can be formed from either polypropylene or polyethylene and the innermost first layer formed from TEFLON.

In general, in another aspect, the invention features a chromatography column including a tubular member having an inlet and outlet end, first and second porous members disposed within the tubular member, and a chromatography or separating media disposed within the tubular member and bounded by the first and second porous members. The tubular member includes an innermost first layer formed from a chemically inert material and a rigid and/or deformable second layer. The second porous member abuts the media and is held firmly by crimping a portion of the tubular member against the second porous member.

Embodiments of the invention may include one or more of the following. The tubular member included in the chromatography column can include a plurality of layers, including at least the innermost first layer formed from the chemically inert material and the rigid, deformable second layer. The second layer can be an intermediate layer and an outermost layer can be formed from the chemically inert material. In one embodiment, the chemically inert material encapsulates the second layer, thereby forming both an innermost first layer and an outermost layer of the chemically inert material.

The first porous member can be in slidable contact with the innermost first layer, and spaced sufficiently from the inlet end to form a module receiving region deep enough for a sample module to be inserted completely into the receiving region.

The first porous member can be held firmly by crimping the column wall against or above the first porous member. The crimped first porous member can be spaced sufficiently from the inlet end to form a module receiving region deep enough for a sample module to be inserted completely into the receiving region. The column wall may be crimped into a grooved region of the first porous member.

The tubular member can further include a sealing region between the inlet end and the module receiving region, the sealing region being sufficiently long to receive a sealing head for making a seal with the inner surface of the tubular member. The tubular member can include a chamfered region near the inlet end.

The second layer can be formed from polypropylene, polyethylene, stainless steel, aluminum, anodized aluminum, acetal, polycarbonate or glass. The innermost first layer can be formed from a fluoropolymer, such as TEFLON, TEFZEL, EFEP or PTFE. In one embodiment the outer layer can be formed from either polypropylene or polyethylene and the innermost first layer formed from TEFLON.

The inlet end of the tubular member can include an inlet tube abutting an upper surface of the first porous member. The inlet tube can have an inner layer formed from a chemically inert material. The chemically inert material can be a fluoropolymer, such as TEFLON, TEFZEL, EFEP or PTFE. The outlet end of the tubular member can include an outlet tube abutting a lower surface of the second porous member. The outlet tube can have an inner layer comprising a chemically inert material. The chemically inert material can be a fluoropolymer, such as TEFLON, TEFZEL, EFEP or PTFE.

In general, in another aspect, the invention features a chromatography column including a tubular member having an inlet and outlet end and first and second porous members disposed within the tubular member. A chromatography or separating media is disposed within the tubular member and bounded by the first and second porous members. The second porous member abuts the media and is held firmly by crimping a portion of the tubular member against the second porous member or into a grooved region of the second porous member.

Embodiments of the invention may include one or more of the following. The first porous member can be in slidable contact with an inner surface of the tubular member, and spaced sufficiently from the inlet end to form a module receiving region. The module receiving region is deep enough for a sample module to be inserted completely into the receiving region.

In another embodiment, the tubular member can be crimped near the inlet end and above the first porous member, such that the first porous member is restrained from sliding above the crimped portion of the tubular member. The crimped portion of the tubular member can be spaced sufficiently from the inlet end to form a module receiving region deep enough for a sample module to be inserted into the receiving region. Alternatively, the first porous member can be held firmly by crimping the tubular member against the porous member or into a grooved region of the first porous member. The crimped first porous member can be spaced sufficiently from the inlet end to form a module receiving region deep enough for a sample module to be inserted completely into the receiving region.

The tubular member can further include a sealing region between the inlet end and the module receiving region, the sealing region being sufficiently long to receive a sealing head for making a seal with the inner surface of the tubular member. The tubular member can further include a chamfered region near the inlet end.

In general, in another aspect, the invention features a chromatography column including a tubular member having an inlet end and an outlet end and first and second porous members disposed within the tubular member and in slidable contact with an inner surface of the tubular member. A chromatography or separating media is disposed within the tubular member and bounded by the first and second porous members. The tubular member is first crimped near the inlet end above the first porous member, such that the first porous member is restrained from sliding above the first crimping. The tubular member is also crimped near the outlet end below the second porous member, such that the second porous member is restrained from sliding below the second crimping. In one embodiment, the first crimping of the tubular member is spaced sufficiently from the inlet end to form a module receiving region deep enough for a sample module to be inserted into the receiving region.

The invention can be implemented to realize one or more of the following advantages. Using two or more layers of materials to form a composite column, the mechanical characteristics of the outer layer, and optionally intermediate layers, can provide structural benefits, such as rigidity, flexibility, deformability and hoop strength, while the properties of the inner layer, such as chemical inertness, can improve chromatographic performance. For example, a composite column having an outer layer formed from polypropylene or polyethylene, and an inner layer formed from a fluoropolymer, is cost-effective and able to achieve high levels of chromatographic performance relative to theoretical maximums, while achieving the necessary structural characteristics.

An inner layer formed from a fluoropolymer increases performance of the chromatography column, because, for example, the fluoropolymer does not interact with a solvent or compound being purified. Due to the higher performance, more concentrated fractions of purified components can be achieved, hence decreasing solvent consumption during the chromatography process.

The physical aspects of the column wall may be determined by the materials used in the outer or intermediate layers of the column wall. Flexible column walls may be used in a pressure vessel to radially compress the column and the chromatographic media within, thereby improving column performance. The combination of the outer, inner, and any intermediate layers may be chosen so that the column wall is deformable, so that it may be crimped, in order to fix a porous member in place, for example. The material for the outer layer may be chosen for its ability to be engraved, embossed, written upon, or otherwise inscribed. The thickness and cross-sectional shape of intermediate layers or the outer layer may be selected for particular physical characteristics, such as strength, flexibility, and durability. The cross-sectional shape of the outer layer may be selected for improved packaging and storage. For example, the cross-sectional shape of the outer layer may be selected to increase the number of columns that can be packed into a minimum space during use or storage. The cross-sectional shape of the outer layer may also be selected in order to include flat surfaces, protrusions, oblong surface(s), or other shapes that will prevent the column from rolling.

Use of beveled or chamfered edges at the inlet end of a composite chromatography column eases insertion of a sealing device, precolumn or sample module into the column. Additionally, beveled or chamfered edges can be advantageous in the manufacturing process, particularly if the composite columns are formed from molding.

The details of one or more embodiments of the invention are set forth in the accompanying drawings and the description below. Other features and advantages of the invention will be apparent from the description, the drawings, and the claims.

DETAILED DESCRIPTION

Figure 1:
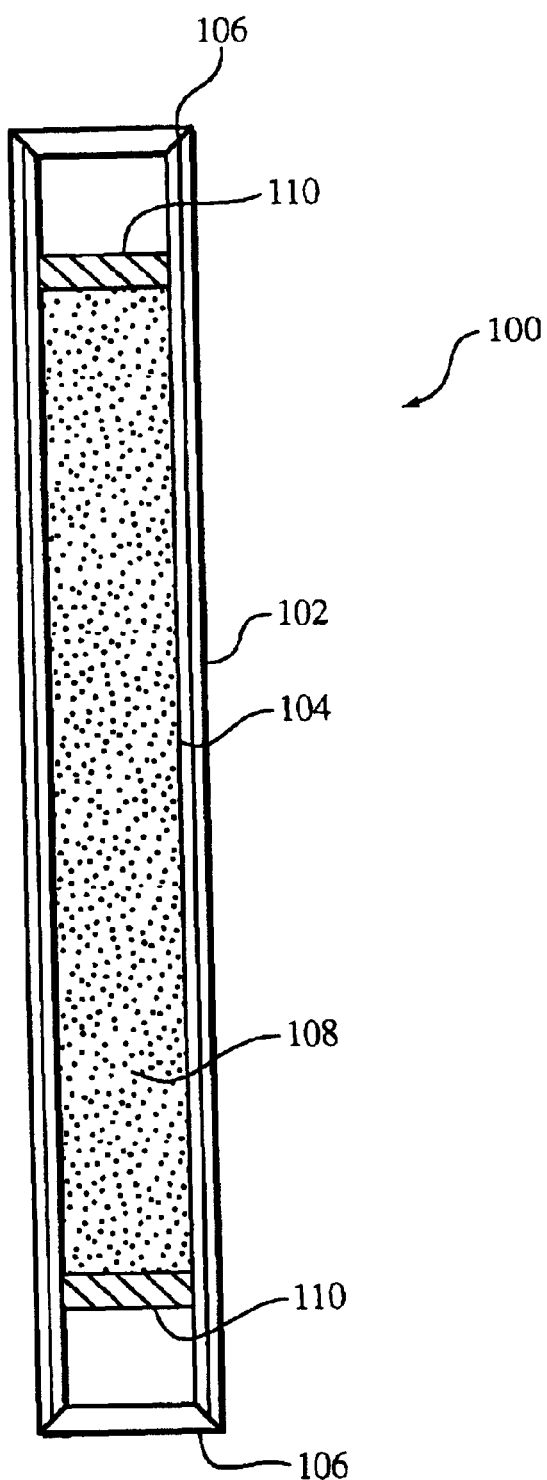
FIG. 1 is a longitudinal cross-sectional view of a chromatography column according to the invention.

Referring to FIG. 1, a chromatography column 100 having layers 102, 104, each terminating at either end of the column 100 with beveled edges 106 is shown. A chromatography media 108 is bounded axially by porous plates 110, which form a stop within the column 100.

The column 100 can be formed from two or more layers, for example, an outer layer 102 and an inner layer 104. Optionally, one or more intermediate layers can be included between the outer layer 102 and the inner layer 104.

The outer layer 102 is a rigid, tubular member. Material for the outer layer 102 is selected for properties desirable to the chromatography column application, for example, hardness, hoop strength, flexibility, deformability and inexpensiveness. Suitable materials for forming the outer layer 102 include plastic, metal, glass or a suitable composite material. Plastic materials exhibiting some or all of the desired properties referred to above include polypropylene, polyethylene, acetal (also known as DELRIN) and polycarbonate. Polypropylene and polyethylene are particularly well suited materials to form the outer layer, since they are able to achieve the required hoop-strength to contain low to medium pressure during the chromatographic process. Suitable metals include stainless steel, steel alloys, aluminum and anodized aluminum.

The material for the inner layer 104 is selected for its superior chromatographic column properties, such as the material's chemical inertness, in that the material does not interact with solvents or compounds being purified. Suitable materials for the inner layer 104 include fluoropolymers such as PTFE, EFEP and materials sold under the trade names TEFLON and TEFZEL.

A column formed of a single layer of pure TEFLON tubing, or another fluoropolymer, may be considered too expensive, particularly for disposable chromatography columns, and would be relatively thick, because thinner layers of fluoropolymers lack the hoop-strength that is necessary to maintain the rigidity of the column. Polypropylene and polyethylene, as discussed above, have the required hoop-strength to form a single layer column, but lack the chemical inertness of a fluoropolymer. As such, polypropylene and polyethylene columns are able to achieve high levels of chromatographic performance, for example, in relation to plate count and asymmetry of peaks, but fall short of the theoretical maximums. By contrast, fluoropolymer columns can attain performance closer to the theoretical maximums.

By using two or more layers of materials to form a column, the mechanical characteristics of the outer layer, and optionally intermediate layers, can provide structural benefits, such as rigidity, flexibility, deformability and hoop strength, while the chemical properties of the inner layer, such as chemical inertness, can improve chromatographic performance. For example, a column 100 having an outer layer 102 formed from polypropylene or polyethylene, and an inner layer 104 formed from a fluoropolymer, is cost-effective and able to achieve high levels of chromatographic performance relative to theoretical maximums, while achieving the necessary structural characteristics.

Figure 2A:
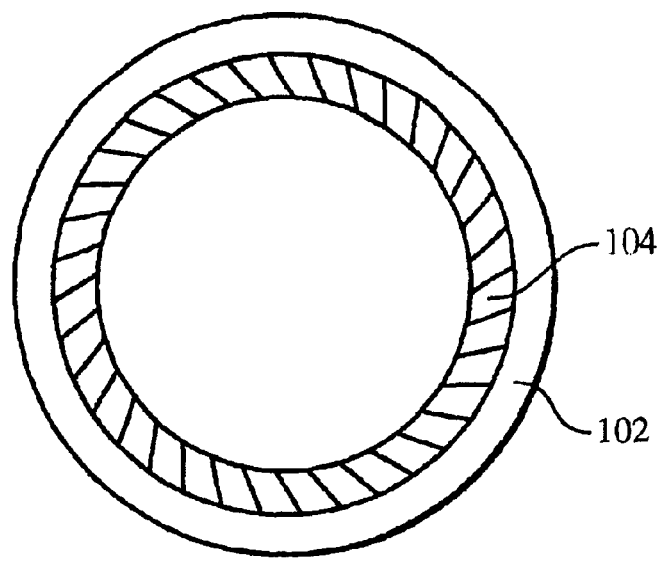
FIG. 2A is a cross-sectional view of a chromatography column.
Figure 2B:
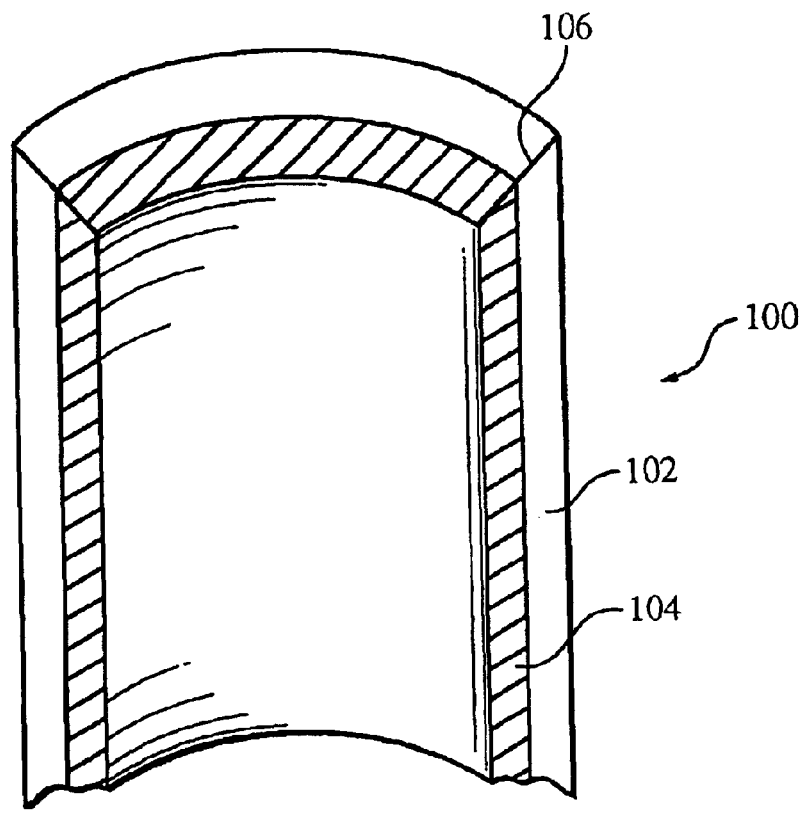
FIG. 2B is a longitudinal cross-sectional view of a portion of the chromatography column of FIG. 2A.

Referring to FIG. 2A and FIG. 2B, a cross-sectional view and partial longitudinal cross-sectional view of column 100 are shown. The inner and outer layers 104, 102 can have any suitable thickness. The outer layer 102 should be at least thick enough to achieve the required hoop-strength. It is often desirable for a chromatography column to have beveled or chamfered edges, so as to ease the insertion of a sealing device, precolumn or sample module into the column. For a composite column having two or more layers all layers may be beveled. For example, the inner and outers layers 104, 102 of column 100 can each run the entire length of the column 100, and terminate on either end with a beveled edge 106, as shown in FIG. 2B.

Figure 3:
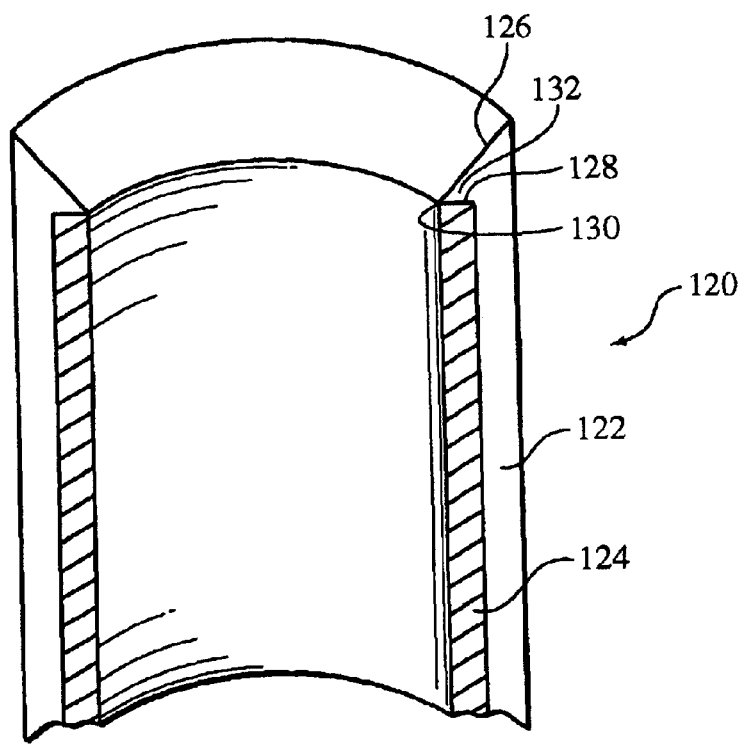
FIG. 3 is a longitudinal cross-sectional view of a portion of a chromatography column.

Referring to FIG. 3, in another embodiment, a column 120 is formed from an outer layer 122 and an inner layer 124. The inner layer 124 terminates at one or both ends (only one end is shown) with a substantially flat surface region 128. The outer layer 122 extends beyond the inner layer 124 and terminates with a beveled edge 126 slanting inwardly until meeting the innermost surface 130 of the inner layer 124, thus forming a lip 132 over the substantially flat surface region 128 of the inner layer 124. This design can be especially advantageous in the manufacturing process, particularly if the column 120 is formed from molding.

Figure 4:
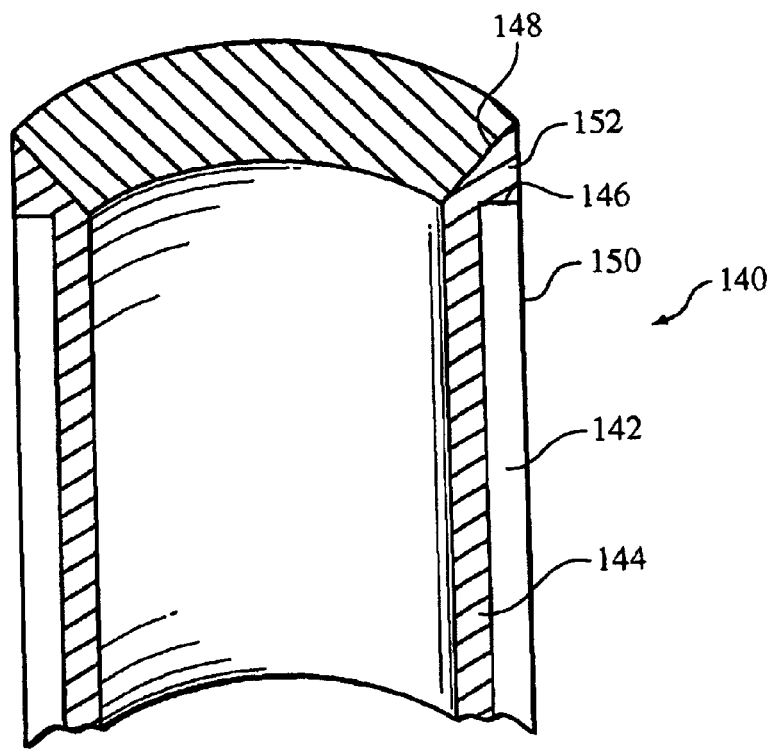
FIG. 4 is a longitudinal cross-sectional view of a portion of a chromatography column.

Referring to FIG. 4, in yet another embodiment, a column 140 is formed from an outer layer 142 and an inner layer 144. The outer layer terminates at one or both ends (only one end is shown) with a substantially flat edge 146. The inner layer 144 extends beyond the outer layer 142 and terminates with a beveled edge 148 slanting outwardly until flush with the outermost surface 150 of the outer layer 142, thus forming a lip 152 over the substantially flat edge 146 of the outer layer 142. As mentioned above in reference to FIG. 3, this design can also be especially advantageous in the manufacturing process, particularly if the column 120 is formed from molding.

Figure 5:
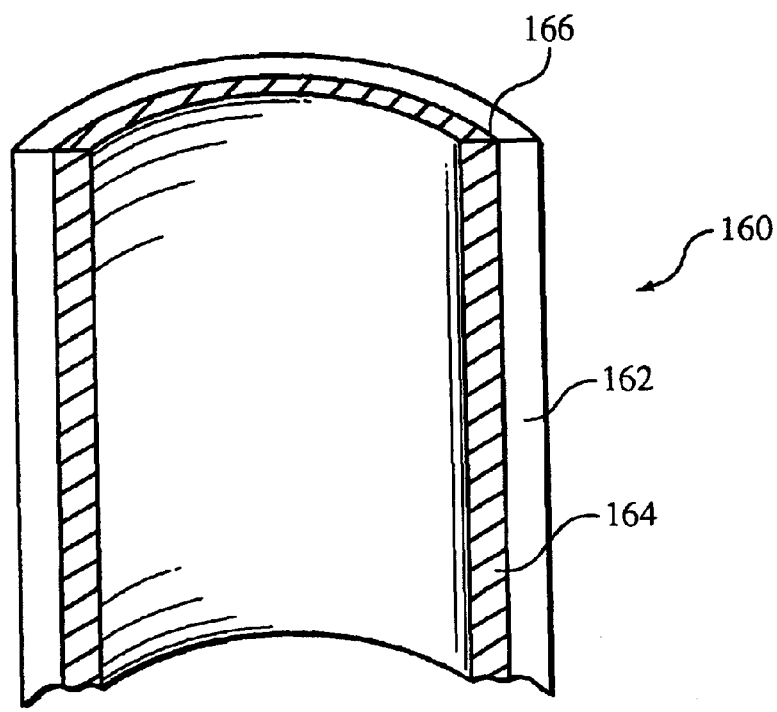
FIG. 5 is a longitudinal cross-sectional view of a portion of a chromatography column.

In another embodiment, as shown in FIG. 5, a column 160 is formed from an outer layer 162 and an inner layer 164, each layer running the entire length of the column 160 and terminating on either end with a substantially flat edge 166.

Alternatively, a column can be formed from two or more layers terminating in any other combination of ends, for example the beveled edge described with reference of FIG. 3 above, can be combined with the flat edge described with reference to FIG. 5 above, wherein one end of the column terminates in a beveled edge and one end terminates in a flat edge. Similarly, the beveled edge of FIG. 4, can be combined with the beveled edge of FIG. 3 or the flat edge of FIG. 5.

Figure 6:
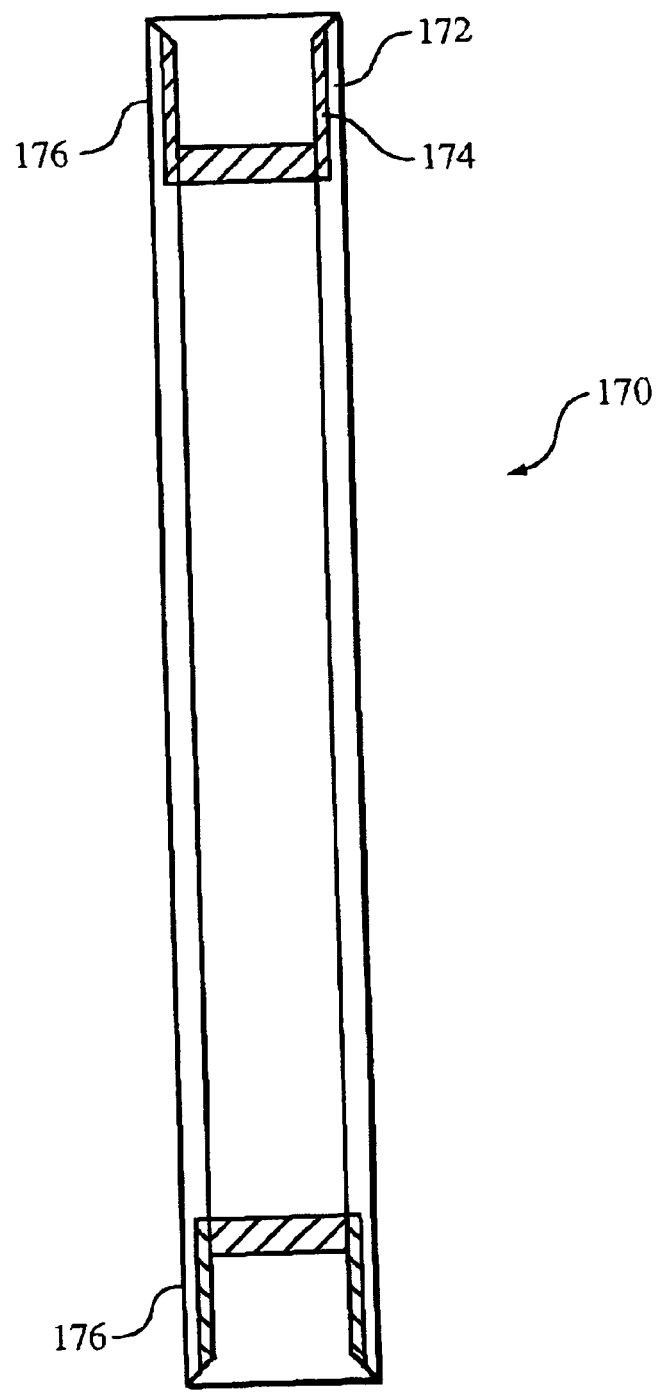
FIG. 6 is a longitudinal cross-sectional view of a chromatography column.
Figure 7:
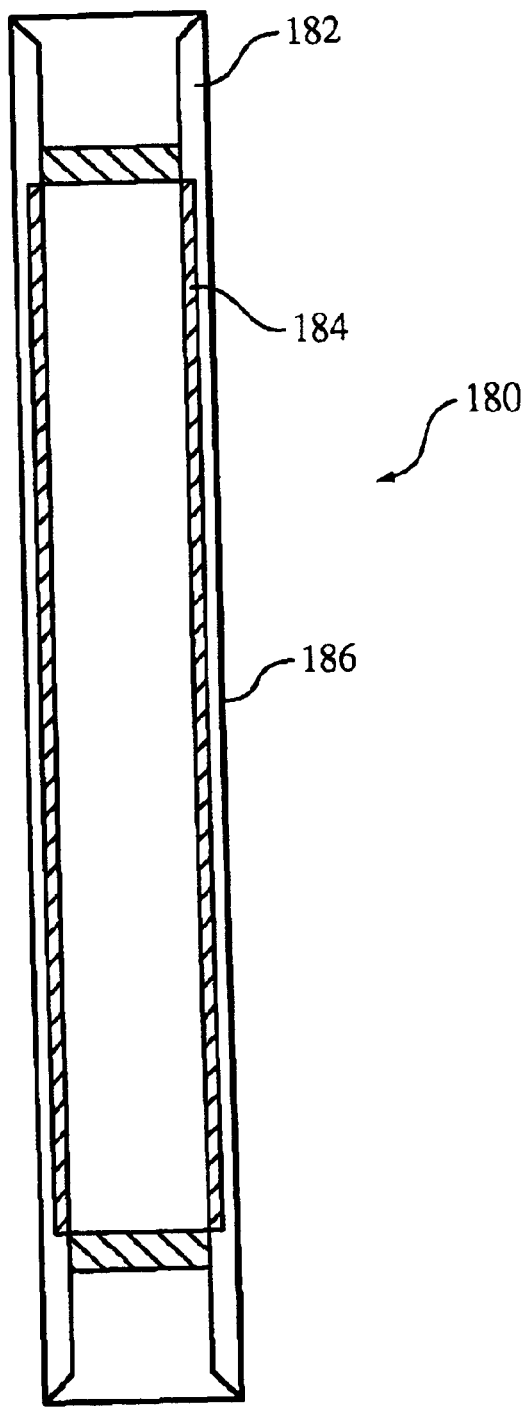
FIG. 7 is a longitudinal cross-sectional view of a chromatography column.

In another embodiment, any of the column layers can be situated at only desired portions of the column, such as a sealing region or a region that contacts the chromatographic media. For example, referring to FIG. 6, a column 170 is shown employing an outer layer 172 that extends the entire length of the column 170 and an inner layer 174 at only the upper and lower sealing regions 176 of the column 170. Alternatively, referring to FIG. 7, a column 180 is shown having an outer layer 182 extending the entire length of the column 180, and an inner layer 184 employed only in the central region 186 of the column 180.

The outer layer and any intermediate layers of a column can have any desired shape. For example, the outer layer 102 of column 100 shown in FIGS. 1, 2A and 2B, is cylindrical, having a substantially circular horizontal cross-section, as shown in FIG. 2A.

Figure 8:
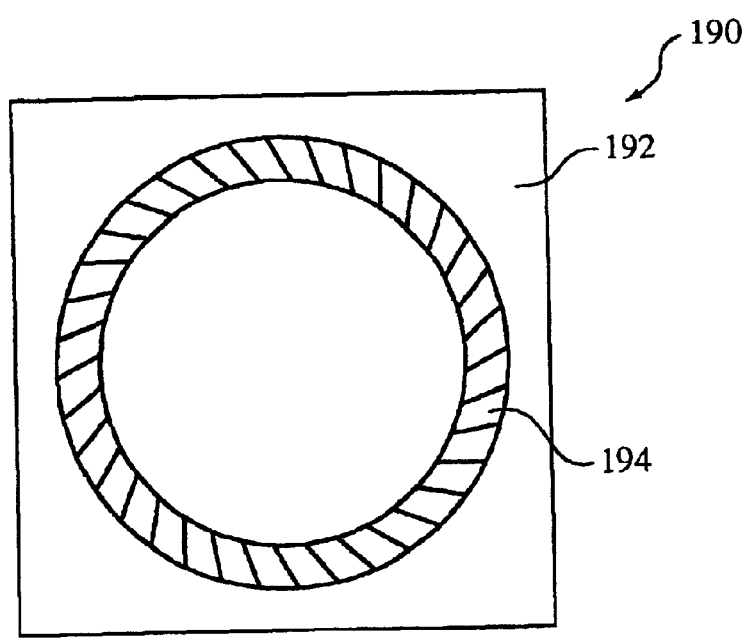
FIG. 8 is a cross-sectional view of a chromatography column having a rectangular outer cross-section and a circular inner cross-section.

In other embodiments, the outer and any optional intermediate layers can have differing horizontal cross-sectional shapes. For example, referring to FIG. 8, the cross-sectional view of a column 190 is shown, having an outer layer 192 and an inner layer 194. The cross-section of the outer layer 192 has a square outer shape and a substantially circular inner shape, while the cross-section of the inner layer 194 is substantially circular. Thus, column 190 has a rectangular, tubular exterior shape and a circular, cylindrical inner shape.

Figure 9:
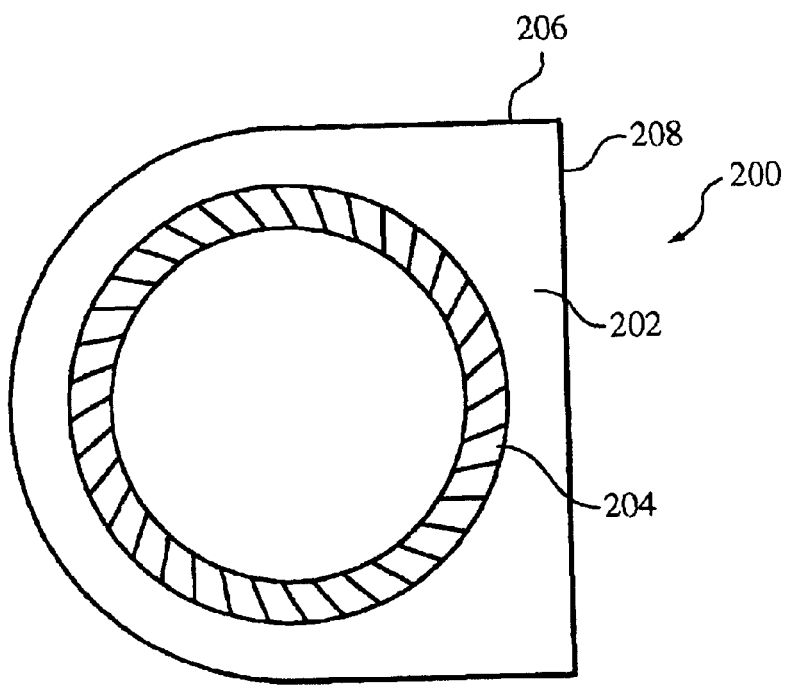
FIG. 9 is a cross-sectional view of a chromatography column having a semi-curved shaped outer cross-section and a circular inner cross-section.

Referring to FIG. 9, a cross-sectional view of a column 200 is shown, having an outer layer 202 and an inner layer 204. The cross-section of the outer layer 202 has a curved outer shape 206 on three exterior sides, at least one flat exterior side 208, and a substantially circular inner shape. The cross-section of the inner layer 204 is substantially circular, thus forming a column 200 with a circular, cylindrical inner shape.

Figure 10A:
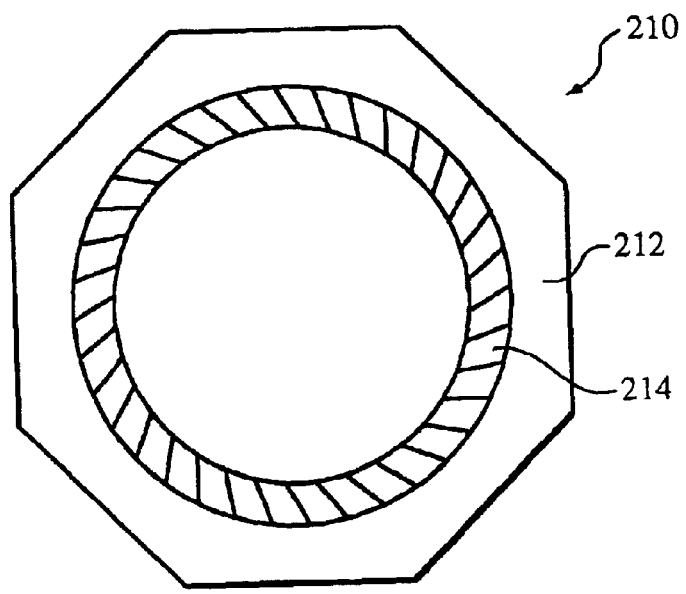
FIG. 10A is a cross-sectional view of a chromatography column having an octagonal outer cross-section and a circular inner cross-section.

FIG. 10A depicts a cross-sectional view of a column 210 having an outer layer 212 with an octagonal exterior cross-sectional shape, and a substantially circular interior cross-sectional shape. The column 210 also includes an inner layer 214, having a substantially circular cross-sectional shape. Thus, the column 210 formed from the outer and inner layers 212, 214, has an octagonal, tubular exterior shape and a circular, cylindrical interior shape.

Figure 10B:
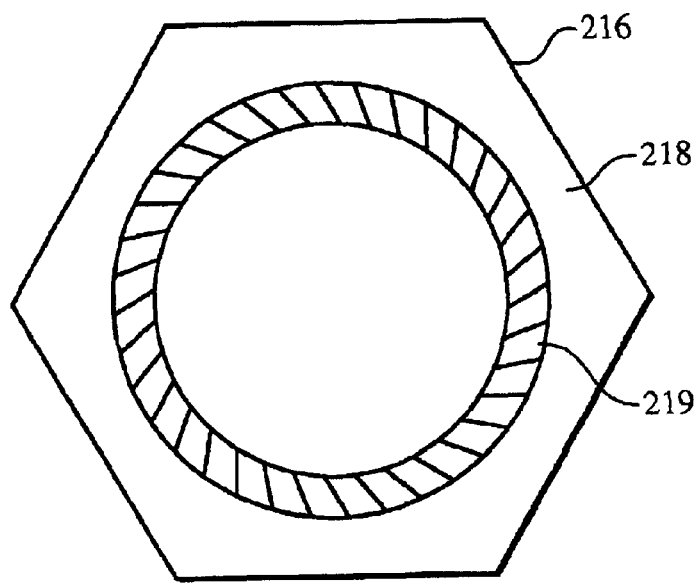
FIG. 10B is a cross-sectional view of a chromatography column having a hexagonal outer cross-section and a circular inner cross-section.

FIG. 10B depicts a cross-sectional view of a column 216 similar to that shown in FIG. 10A, but having an outer layer 218 with a hexagonal exterior cross-sectional shape. The interior cross-sectional shape is substantially circular. The column includes an inner layer 219, also having a substantially circular cross-sectional shape. The column formed from the outer and inner layers 218, 219 has a hexagonal, tubular exterior shape and a circular, cylindrical interior shape.

Figure 11:
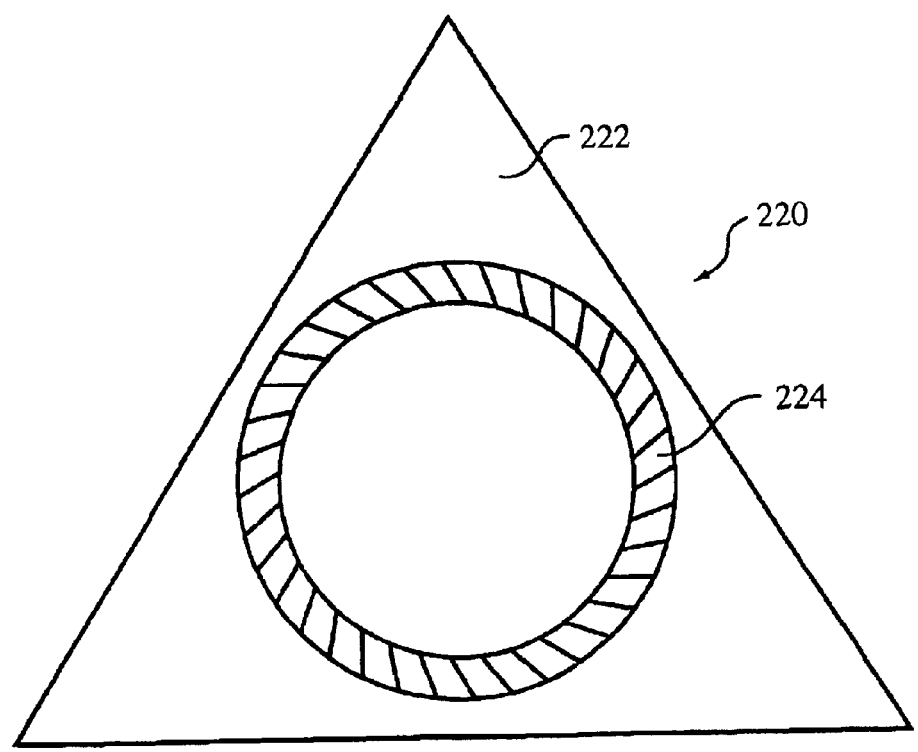
FIG. 11 is a cross-sectional view of a chromatography column having a triangular outer cross-section and a circular inner cross-section.

As shown in FIG. 11, a column 220 can be formed from an outer layer 222 having a triangular exterior cross-sectional shape and a substantially circular interior cross-sectional shape, and an inner layer 224 having a substantially circular interior cross-sectional shape. The column 220 thus has a three-sided, tubular exterior surface and a cylindrical inner surface.

Figure 12:
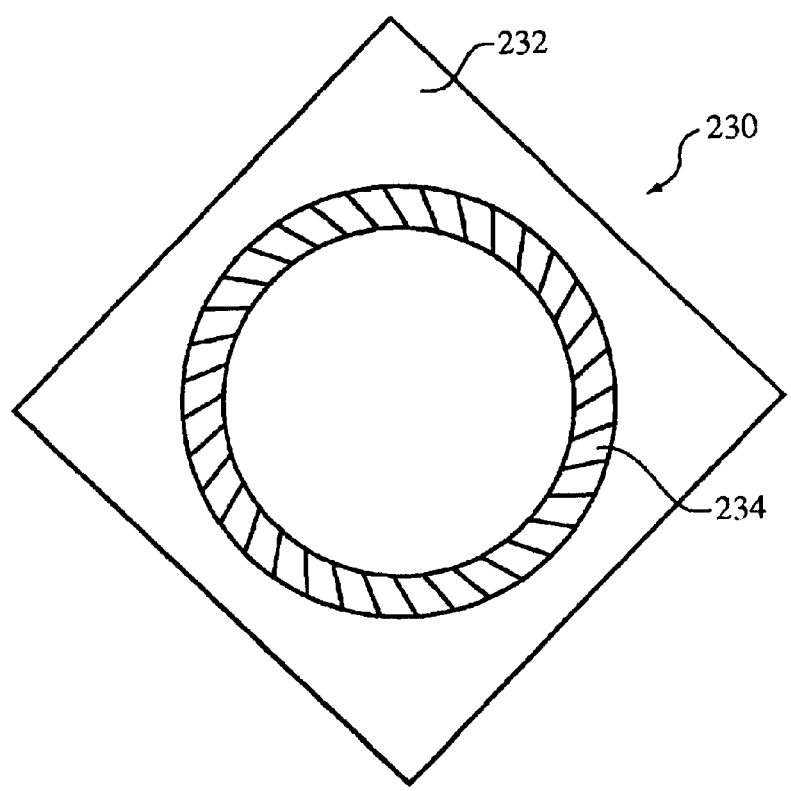
FIG. 12 is a cross-sectional view of a chromatography column having a diamond-shaped outer cross-section and a circular inner cross-section.

Referring to FIG. 12, a column 230 can be formed from an outer layer 232 having a diamond-shaped exterior cross-section and a substantially circular interior cross-section, and an inner layer 234 having a substantially circular interior cross-section. The column 230 thus has a four-sided, tubular exterior surface and a cylindrical inner surface.

In another embodiment, the inner layer can have an exterior cross-sectional shape differing from the inner cross-sectional shape of the inner layer. Any number of other embodiments are also possible, having any number of combinations of inner, outer and intermediate cross-sectional shapes. An outer layer shape can be selected to advantageously allow for a maximum number of columns to be packed into a minimum space during use or for storage or to prevent a column from rolling, when set on a surface.

Figure 13:
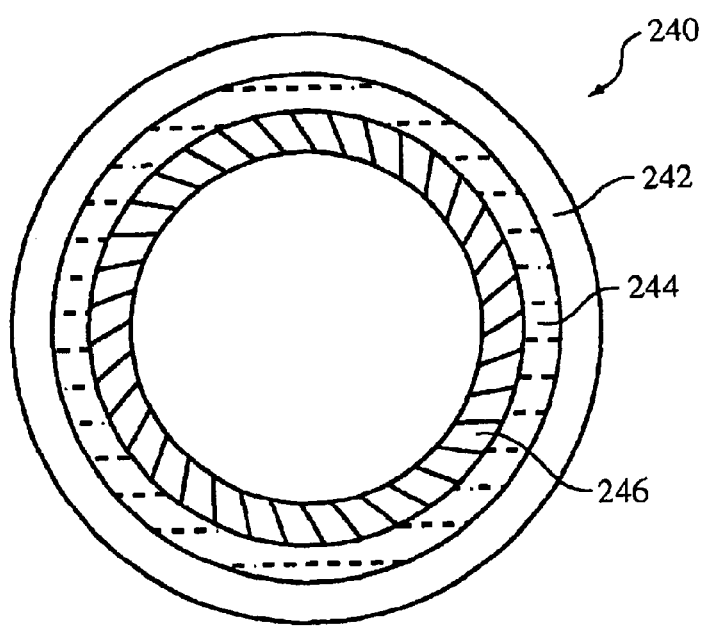
FIG. 13 is a cross-sectional view of a chromatography column having three composite layers.

A composite column can be formed with one or more intermediate layers in between an outer layer and an inner layer. For example, referring to FIG. 13, a cross-sectional view of a column 240 is shown, the column 240 including an outer layer 242, an intermediate layer 244 and an inner layer 246. Material for an intermediate layer can be selected to exhibit desirable properties similar to those discussed above in reference to the outer layer, i.e. hardness, hoop-strength, flexibility and deformability. Alternatively, an intermediate layer can be used to form a bond between two layers, for example, the outer layer and the inner layer. In this instance, the intermediate layer could be an adhesive material used to bind the inner and outer layers together.

Figure 14A:
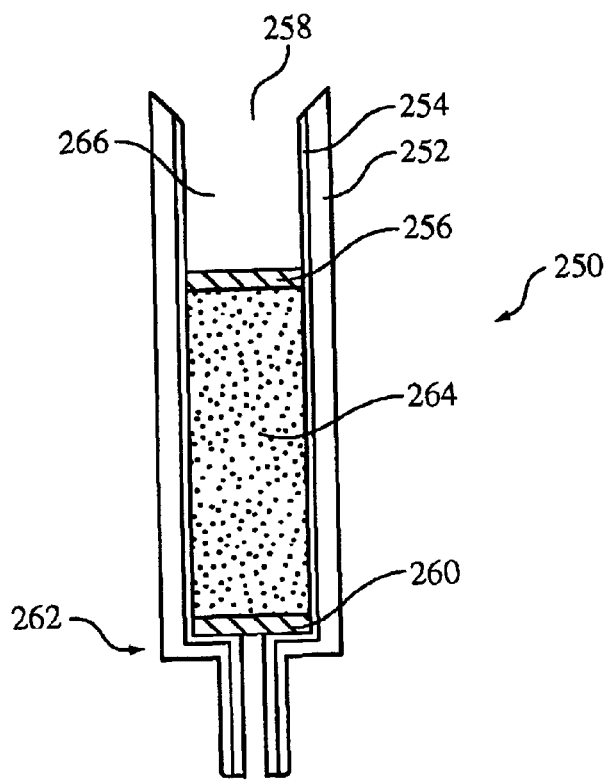
FIG. 14A is a longitudinal cross-sectional view of a composite chromatography column having a slidable upper porous plate.

The porous plates positioned within a chromatography column can be held firmly in place by convenient means, or can be slidable along the interior of the inner layer of a composite column. Referring to FIG. 14A, a composite column 250 is shown, including an outer layer 252 and an inner layer 254, and can optionally include one or more intermediate layers. An upper porous plate 256 is situated near an inlet end 258 of the column 250, and a lower porous plate 260 is situated near an outlet end 262 of the column 250. A chromatography or a separation media 264 is bounded between the upper and lower porous plates 256, 260.

Figure 14B:
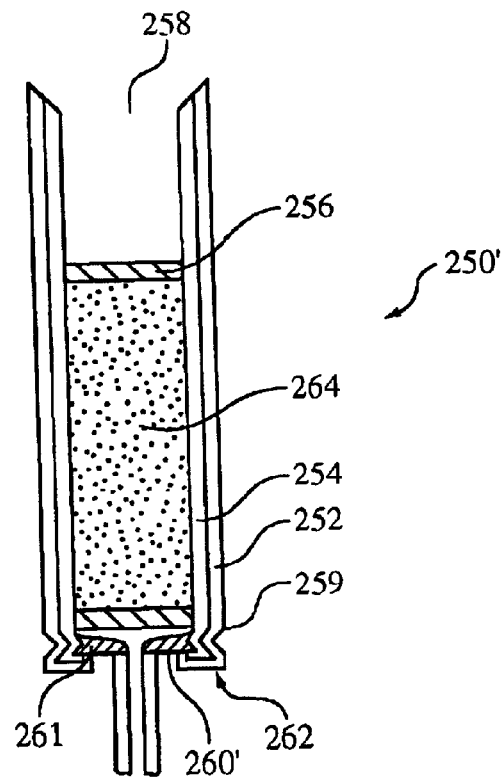
FIG. 14B is a longitudinal cross-sectional view of a composite chromatography column having a slidable upper porous plate and a crimped lower porous plate.

In this embodiment, the upper porous plate 256 is in slidable contact with the inner layer 254. The upper porous plate 256 is spaced sufficiently from the inlet end 258 to define a module receiving region 266 for receiving a sample module entirely within the column 250. The lower porous plate 260 may be in slidable contact with the inner layer 254. As shown in FIG. 14B, in another embodiment 250', the lower porous plate 260' may alternatively be held firmly in place near the outlet end 262, for example, by crimping the outer layer 252 so that the inner layer 254 presses against the lower porous plate 260'. The lower porous plate 260' may have a grooved region 261 for receiving the crimped portion 259 of the composite column 250'. In another embodiment 250", shown in FIG. 14C, the upper porous plate 256' and lower porous plate 260' can both be held firmly in place, for example, by crimping the outer layer 252 so that the inner layer 254 presses against the upper and lower porous plates 256', 260'.

Figure 14C:
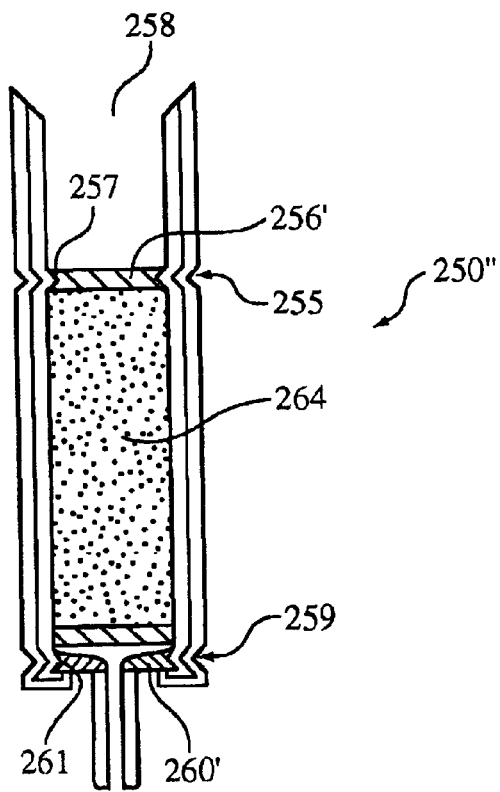
FIG. 14C is a longitudinal cross-sectional view of a composite chromatography column having crimped upper and lower porous plates.
Figure 14D:
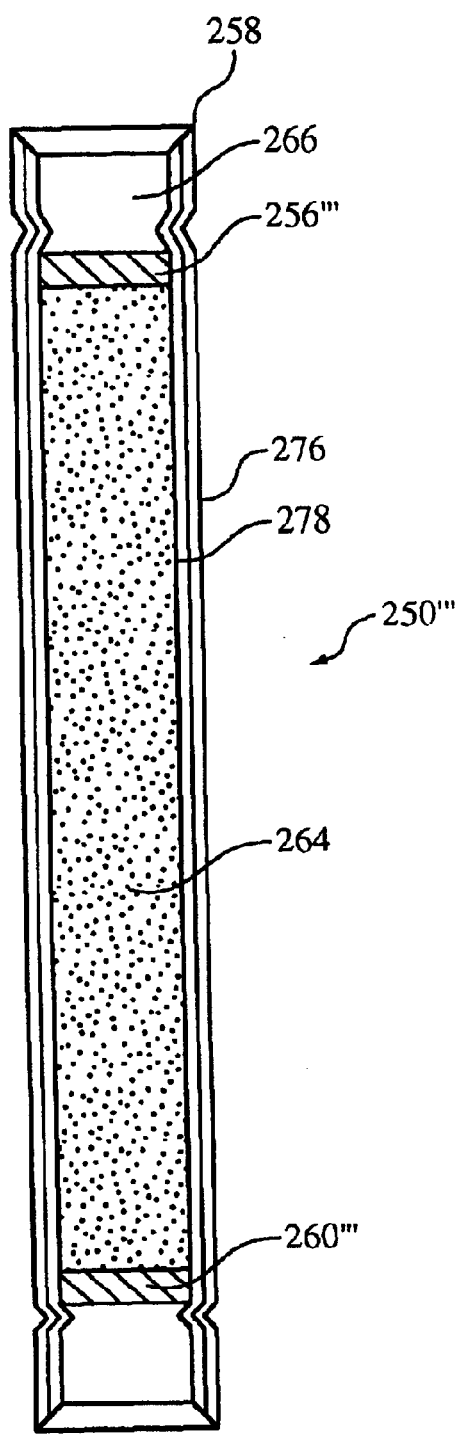
FIG. 14D is a longitudinal cross-sectional view of a composite chromatography column having a crimp in the column above the upper porous plate and below the lower porous plate.

Another embodiment 250''' is shown in FIG. 14D, with the column crimped above upper porous plate 256''' and below lower porous plate 260'''. The upper and lower porous plates 256''', 260''' remain slidable relative to the inner layer of the column wall 278, but are retained by the crimped portion of column 250''' at a maximum upper and lower position, respectively. In this way, column 250''' may be filled with media 264, crimped above and below upper and lower porous plates 256''', 260''' respectively, and the media 264 may be further compressed as needed if media 264 settles (e.g., during shipping or use). By positioning the crimping sufficiently below the inlet end 258, a module receiving region 266 can be defined for receiving a sample module entirely within the column 250'''.

The crimping feature shown in FIGS. 14B–14D can also be used with a chromatography column formed of a single layer, rather than a composite column. Crimping a column on or above a porous member or plate may reduce the exactness of the tolerances required in order to achieve the desired fit between the porous member and the column wall. Crimping is an effective way to fix or retain a porous member within a column and may prove more efficient and less expensive that techniques such as milling or molding a column with an internal rim, projection, or stop.

The crimping feature may be employed with a deformable metal column, such as aluminum, anodized aluminum, stainless steel, or any other metal, or crimping may also be performed with a plastic column and may be accomplished by deforming a tube with or without the use of heat, as well as pressure. For example, a cylindrical plastic tube may be formed by extrusion and then heat-molded, in order to form a crimped region.

Figure 15:
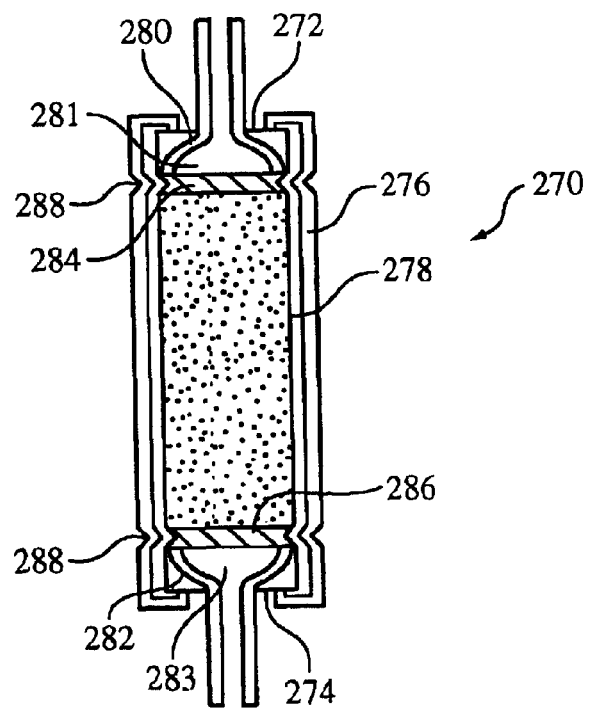
FIG. 15 is a longitudinal cross-sectional view of a composite chromatography column having an inlet tube and an outlet tube.

Referring to FIG. 15, in another embodiment, a composite chromatography column 270 can include an inlet member 272 and an outlet member 274 at either end of the column 270. The column 270 includes an outer layer 276 and an inner layer 278, and can optionally include one or more intermediate layers. The inlet member 272 includes an inner layer 280 formed from a chemically inert material, for example, a material such as was described above in reference to an inner layer of a composite column. The outlet member 274 also includes an inner layer 282 formed from such a chemically inert material. Alternatively, the inlet and outlet tubes 272, 274 can be a single layer formed entirely from a chemically inert material (for example, a fluoropolymer, such as TEFLON, TEFZEL, EFEP or PTFE), or from any other suitable material such as, for example, polypropylene, polyethylene, stainless steel, aluminum, anodized aluminum, acetal, polycarbonate or glass.

The inlet member 272 abuts an upper porous plate 284, and the outlet tube 274 abuts a lower porous plate 286. The inlet member 272 forms a flow distribution region 281 adjacent to the upper porous plate 284. Similarly, the outlet member 274 forms a flow collection region 283 adjacent to the lower porous plate 286. Flow can be introduced into the column 270 through the narrow portion of the inlet member 272 and released from the column 270 through the narrow portion of the outlet member 274. A chromatography or separation media is axially bound between the upper and lower porous plates 284, 286. The upper and lower porous plates 284, 286 are held firmly in place, for example, by crimping the outer and inner layers 276, 278 of the column 270 into a grooved region 288 of either plate.

Referring again to FIG. 14C, an outlet member 263 is shown. The outlet member 263 depicted in FIG. 14C is integral to the lower porous plate 260', that is, together they form a single unit, as contrasted to the outlet member 274 and lower porous plate 286 shown in FIG. 15. The outlet member 263 can be lined with a chemically inert material. The inlet member 272 shown in FIG. 15 can similarly be configured such that the inlet member 272 and upper porous plate 284 are an integral unit.

A number of other embodiments are also possible. For example, a composite column can include an upper porous plate in slidable contact with an inner layer of the column, and sufficiently spaced from an inlet end of the column to define a module receiving region for receiving a sample module, and a lower porous plate abutting an outlet tube, the lower porous plate held firmly in place by crimping an outer layer of the column into a grooved region of the plate. Alternatively, the upper porous plate can be held firmly in place by crimping the outer layer of the column into a grooved region of the upper plate, rather than being slidable.

Referring to FIGS. 14B and 14D, the upper and lower porous plates 256, 260 can be spaced from the ends of the column 250 to provide inlet and outlet regions. For example, in FIG. 14B, the upper porous plate 256 is spaced below the inlet end 258 to define a module receiving region 266, and the lower porous plate 260' is substantially flush with the outlet end of the column. As shown in FIG. 14D, in another embodiment the lower porous plate 260'" may be spaced above the outlet end to form an outlet region. In other embodiments the upper and lower porous plates may be spaced at different distances from their respective ends of the column. For example, an inlet region defined by the positioning of the upper porous plate may be substantially longer than an outlet region defined by the positioning of the lower porous plate. In another embodiment, both the upper and lower porous plates can be substantially flush with their respective ends of the column.

A composite column including two or more layers can be manufactured by any convenient process. For example, a co-extrusion process or a co-molding process, where the two or more layers are formed together.

Alternatively, a first layer can be formed, for example by extrusion or molding, and a second layer added to the exterior surface or interior surface of the first layer by any convenient means, including coating, vacuum forming and thermal bonding. This process can be repeated to add any number of additional composite layers.

Another alternative method of manufacture includes independently forming a first and second layer, for example by extrusion or molding, and affixing the first and second layer to one another using an adhesive intermediate layer. For example, an adhesive layer can be applied to the exterior surface of a first layer. A second layer can then be positioned about the exterior surface of the first layer, and held in place by the adhesive intermediate layer.

In yet another method of manufacture, a first layer can be formed, for example by extrusion or molding, and then encapsulated by a material forming the second layer, such that the innermost layer and outermost layer are formed from the second material, and a middle or intermediate layer is formed from a first material. For example, the first layer may be formed from a rigid material such as polyethylene, which is then encapsulated by a second material, such as TEFLON. The resulting column has an innermost layer of TEFLON, a middle layer of polyethylene and an outermost layer of TEFLON. This mode of manufacture can be used to manufacture any of the embodiments discussed above, in which case the layer referred to above as the 'outer layer', would in fact form an intermediate layer, as the outermost layer would be formed from the encapsulation material, also forming the innermost layer.

The outer layer can be formed from a deformable material and/or a rigid material. For example, the outer layer can be formed from polypropylene, polyethylene, stainless steel, aluminum, anodized aluminum, acetal, polycarbonate or glass. The inner layer can be formed from a chemically inert material. For example, the inner layer can be formed from a fluoropolymer, such as TEFLON, TEFZEL, EFEP (ethylene-fluorinated ethylene-propylene) or PTFE. The inner layer can be a lining, sleeve, or cladding. The inner layer may be impregnated in the outer layer or may be formed by, coating, co-extrusion, anodizing, or bonding. Inner layers of TEFLON or like materials may be formed by TEFLON hardcoating or a similar technique. Forming an inner layer of TEFLON on an aluminum outer layer or intermediate layer surface through TEFLON hardcoating is an exemplary technique. The inner layer can also be formed from a deformable material and/or a rigid material. In one embodiment, the outer layer can be formed from polypropylene and the inner layer formed from TEFLON.

The composite column designs described herein may be used in any desired chromatography device or method, including all of the chromatography devices and methods described herein and all of the devices and methods described in U.S. patent application Ser. No. 08/968,287 filed Nov. 12, 1997 (now U.S. Pat. No. 6,086,766), U.S. patent application Ser. No. 09/137,019 filed Aug. 20, 1998 (now U.S. Pat. No. 6,132,605), U.S. patent application Ser. No. 09/137,278 filed Aug. 20, 1998 (now U.S. Pat. No. 6,139,733), U.S. patent application Ser. No. 09/548,214 filed Apr. 12, 2000 (now U.S. Pat. No. 6,221,252), U.S. patent application Ser. No. 09/548,261 filed Apr. 12, 2000 (now U.S. Pat. No. 6,294,087), and pending U.S. patent application Ser. No. 09/687,801, filed Oct. 13, 2000. All of these applications and patents are incorporated herein by reference.

Figure 16:
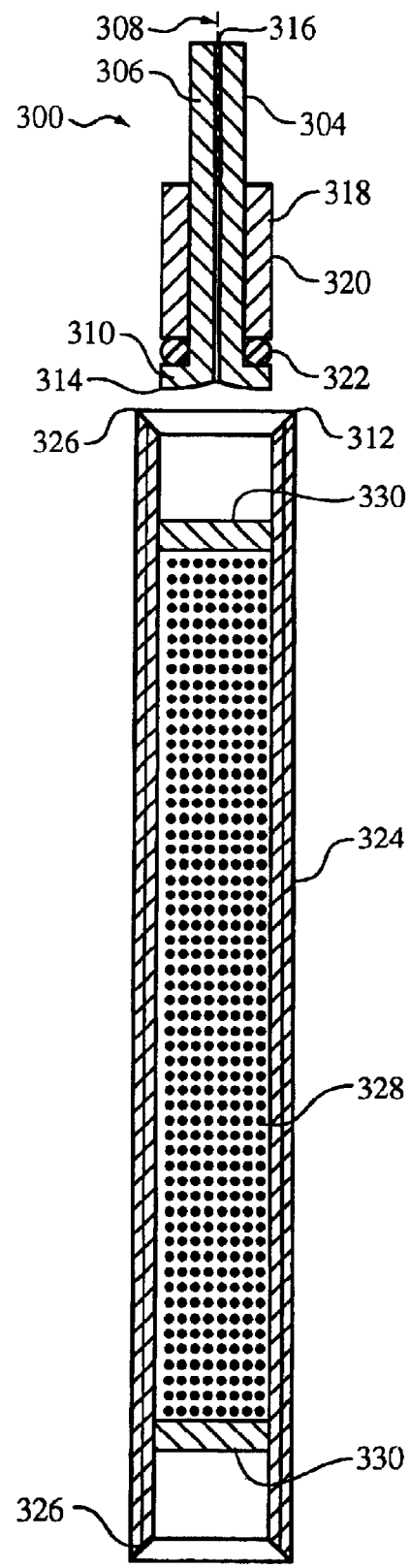
FIG. 16 is a longitudinal cross-sectional view of a sealing apparatus and a chromatography column.
Figure 17:
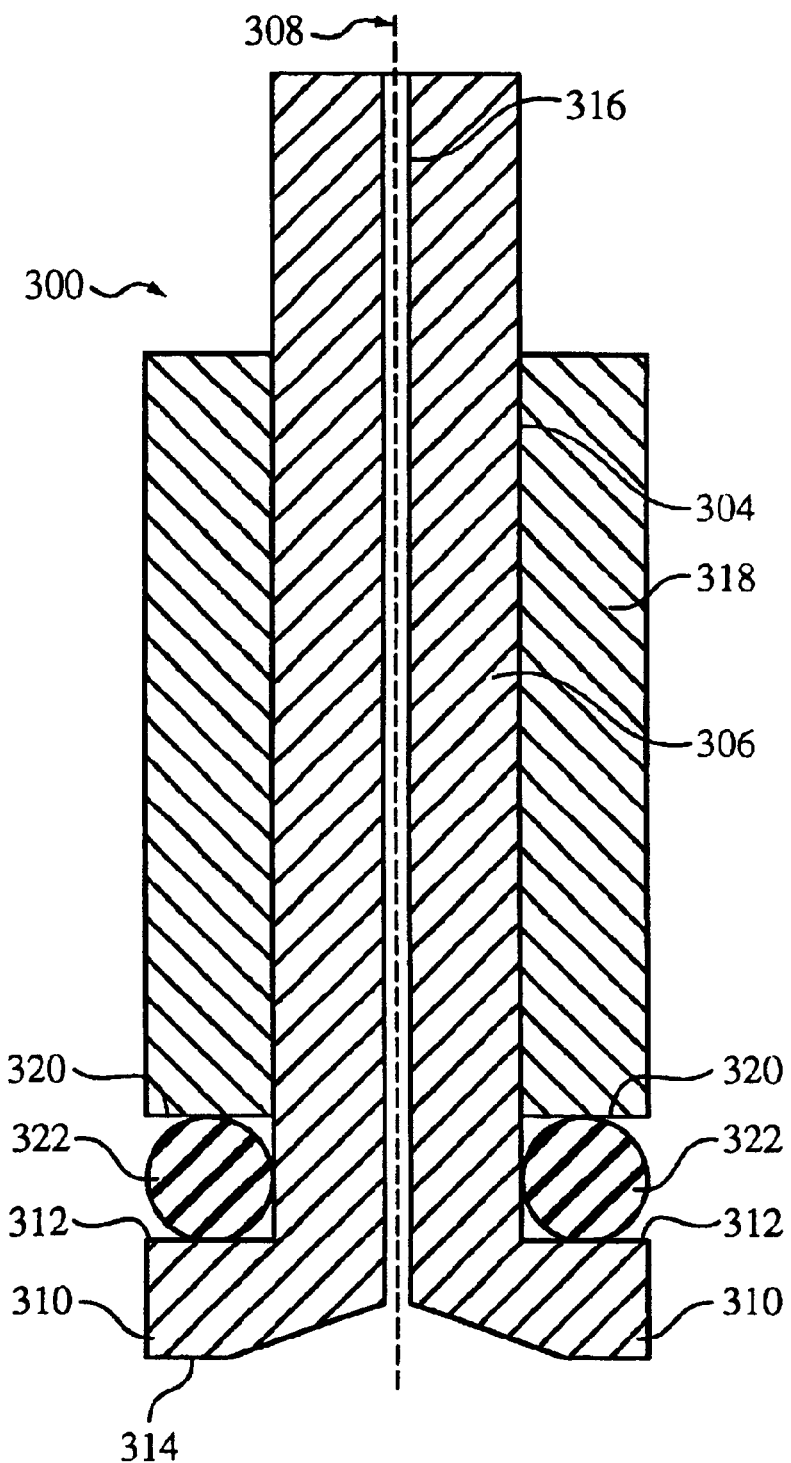
FIG. 17 is a longitudinal cross-sectional view of a sealing apparatus.
Figure 18:
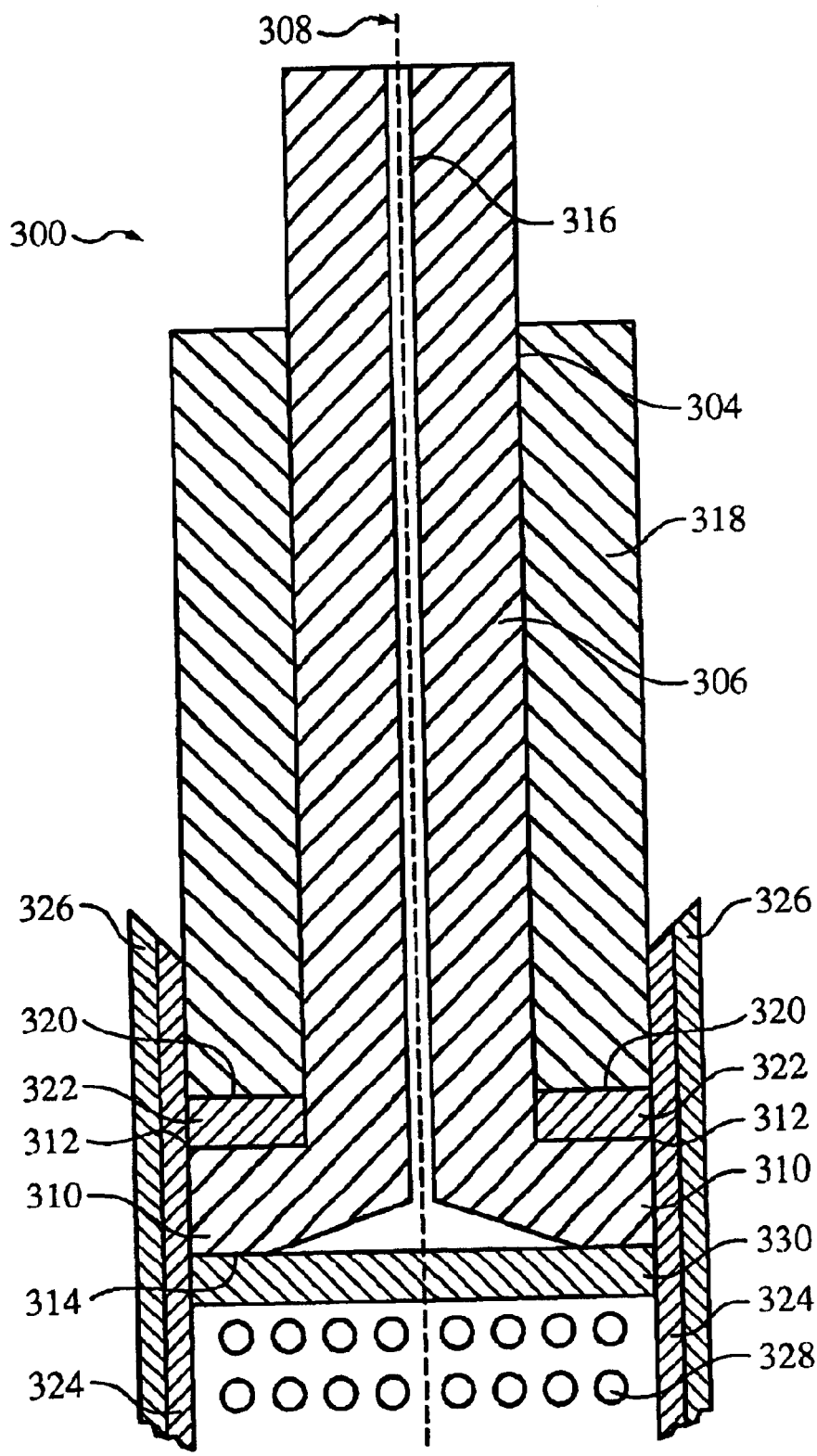
FIG. 18 is a longitudinal cross-sectional view of a sealing apparatus showing the formation of a seal with a chromatography column.

In one embodiment, a composite chromatography column as described above can be used in a liquid chromatography apparatus as follows. Referring to FIGS. 16–18, there is shown a sealing apparatus employing sealing head 300, which includes first head piece 304, having body 306 with longitudinal axis 308. First head piece 304 has outwardly-extending shoulder 310, first compression face 312 that is located on shoulder 310, and contact face 314. Part of contact face 314 has a slightly conical shape or other concavity (exaggerated in FIGS. 17 and 18). First head piece 304 defines flow path 316 along axis 308. Second head piece 318, which includes second compression face 320 and a compression force receiving member extending thereabove, is sized to slidably receive body 306 of first head piece 304. Elastomeric sealing member 322 is at least partially situated between first compression face 312 and second compression face 320.

Sealing head 300 and its components are sized to fit slidably into composite column 324, having chamfered edges 326, and chromatography media 328 bounded axially by porous plates 330 which form a rigid stop within the column. The composite column 324 is formed from an outer layer 332 and an inner layer 334. Materials for the outer and inner layers 332, 334 are selected as described above. Alternatively, the composite column 324 can include one or more intermediate layers between the outer layer 332 and inner layer 334.

The connection of the apparatus is shown in FIGS. 16 and 18. As shown in FIG. 16, first head piece 304, elastomeric sealing member 322, and second head piece 318 are oriented so that they may slide into composite column 324. As shown in FIG. 18, after first head piece 304, elastomeric sealing member 322, and second head piece 318 are situated within composite column 324, and contact face 314 is stopped at porous plate 330, additional downward force on second head piece 318 causes first head piece 304 and second head piece 318 to be moved toward each other, thus axially compressing elastomeric sealing member 322 between first compression face 312 and second compression face 320. The axial compression of elastomeric sealing member 322 causes it to expand laterally and press against composite column 324, thus forming a seal.

As shown in FIG. 18, insertion of sealing head 300 can create a close connection between contact face 314 and porous plate 330. Compressing elastomeric sealing member 322 between first compression face 312 and second compression face 320, by pressing second head piece 318 against elastomeric sealing member 322, which in turn presses first head piece 304 against porous plate 330, can maintain a close connection between contact face 314 and porous plate 330 while forming a seal between sealing head 300 and composite column 324.

In one combination, sealing head 300 is used to seal composite column 324 having flexible walls. In other combinations, sealing head 300 is part of a containment structure assembly for receiving composite column 324. The containment structure assembly may be pressurizable, such as a pressure vessel assembly that receives composite column 324, compresses the flexible walls of composite column 324, and provides uniform packing for chromatography media 328 therein. A containment structure of this type is discussed in U.S. Pat. No. 4,250,035 to McDonald, et al., which is incorporated herein by reference. Another type of pressurizable containment structure is discussed in U.S. Pat. No. 5,601,708 to Leavesley, which is also incorporated herein by reference. In other combinations, sealing head 300 is used to seal composite column 324 having rigid walls.

The radial displacement of the outer surface of elastomeric sealing member 322 accommodates a range of inner diameters of composite column 324, permitting effective seals while relaxing tolerances for the inner diameter of composite column 324 to ±0.005".

Figure 19A:
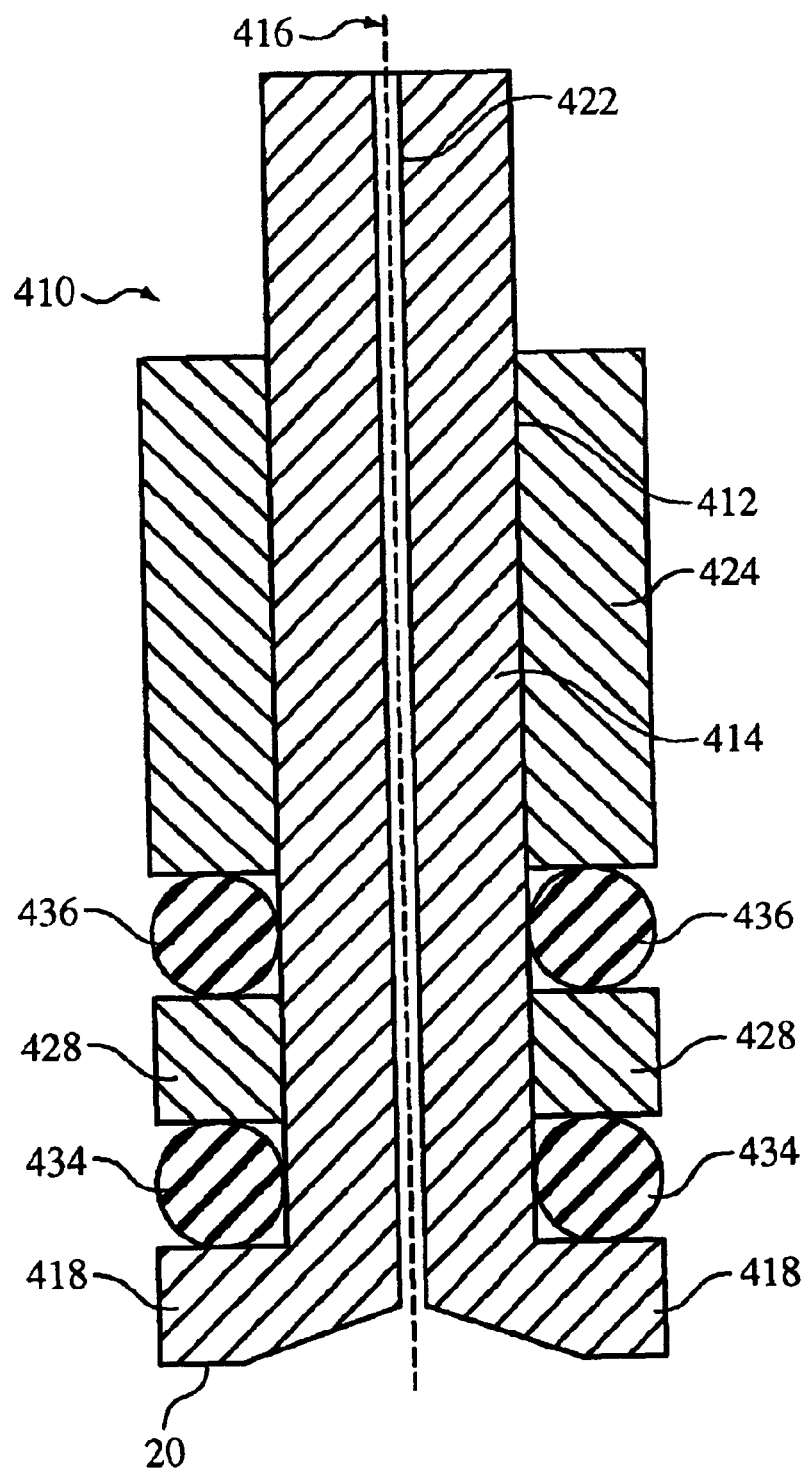
FIG. 19A is a longitudinal cross-sectional view of a sealing apparatus.
Figure 19B:
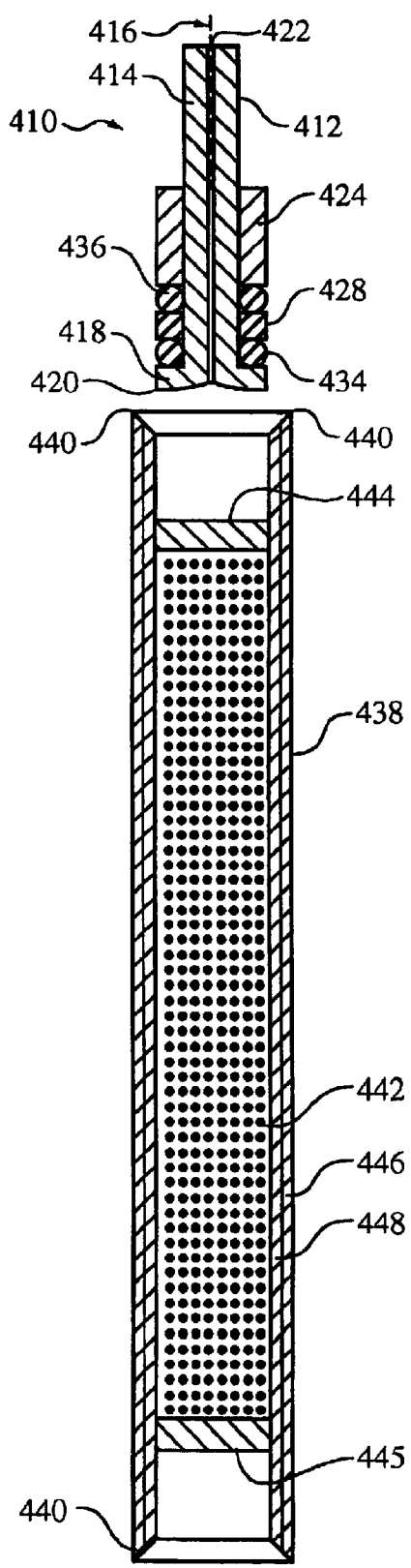
FIG. 19B is a longitudinal cross-sectional view of a sealing apparatus and a chromatography column.
Figure 19C:
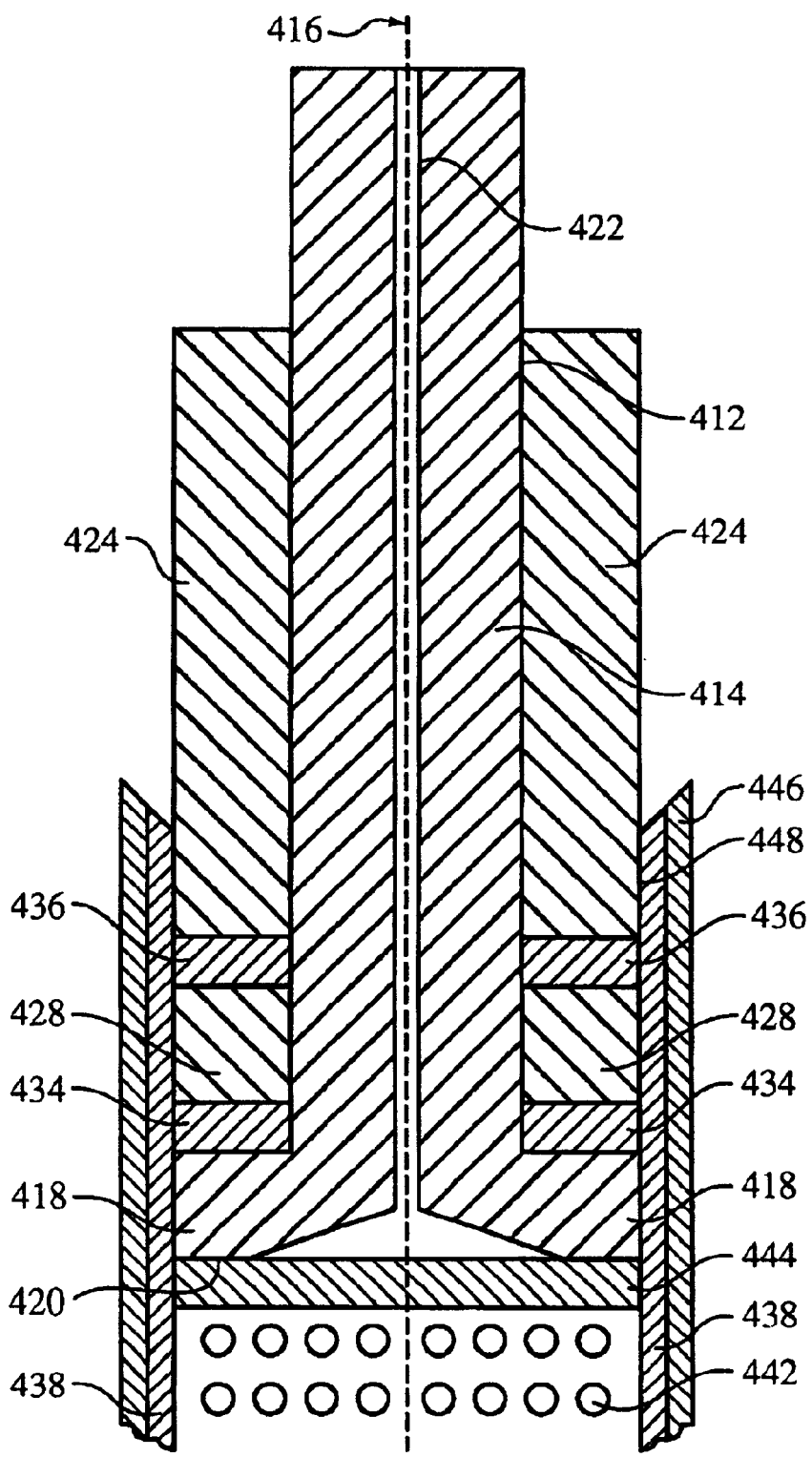
FIG. 19C is a longitudinal cross-sectional view of a sealing apparatus showing the formation of seals with a chromatography column.

Referring to FIGS. 19A–19C, there is shown an alternate embodiment of a sealing apparatus employing sealing head 410, which includes first head piece 412, second head piece 424, intermediate head piece 428, and first and second annular elastomeric sealing members 434, 436.

First head piece 412 has body 414 with longitudinal axis 416. First head piece 412 has outwardly extending shoulder 418, and contact face 420. Part of contact face 420 has a slightly conical shape or other concavity. First head piece 412 defines flow path 422 along axis 416.

Body 414 of first head piece 412 fits slidably through second head piece 424, intermediate head piece 428, and through first and second elastomeric sealing members 434, 436.

First elastomeric sealing member 434 is adjacent to both shoulder 418 and intermediate head piece 428. Second elastomeric sealing member 436 is adjacent to both intermediate head piece 428 and second head piece 424.

Sealing head 410 and its components are sized to fit slidably into composite column 438, having an outer layer 446 and an inner layer 448 having chamfered edges 440. The composite column 438 can optionally include one or more intermediate layers, as described above. Material can be selected for the outer layer 446, inner layer 448 and optional intermediate layers as described above. Composite column 438 is filled with chromatography media bed 442, which is bounded axially by porous plates 444, 445.

The connection of the apparatus is shown in FIGS. 19B and 19C. As shown in FIG. 19B, first head piece 412, second head piece 424, intermediate head piece 428, and elastomeric sealing members 434, 436 are oriented so that they may slide into composite column 438. As shown in FIG. 19C, after sealing head 410 is situated within composite column 438, first head piece 412 and second head piece 424 are moved relative to each other. This relative movement axially compresses first elastomeric sealing member 434 between shoulder 418 and intermediate head piece 428 and also compresses second elastomeric sealing member 436 between intermediate head piece 428 and second head piece 424. The axial compression of elastomeric sealing members 434, 436 causes them to expand laterally and press against the interior surface of composite column 438, thus forming seals.

As shown in FIG. 19C, insertion of sealing head 410 can create a close connection between contact face 420 and porous plate 444. Compressing elastomeric sealing members 434, 436, by pressing second head piece 424 against second elastomeric sealing member 436, which in turn presses second elastomeric sealing member 436 against intermediate head piece 428, intermediate head piece 428 against first elastomeric sealing member 434, first elastomeric sealing member against shoulder 418, and contact face 420 against porous plate 444, can maintain a close connection between contact face 420 and porous plate 444 while forming a seal between sealing head 410 and composite column 438.

Figure 20:
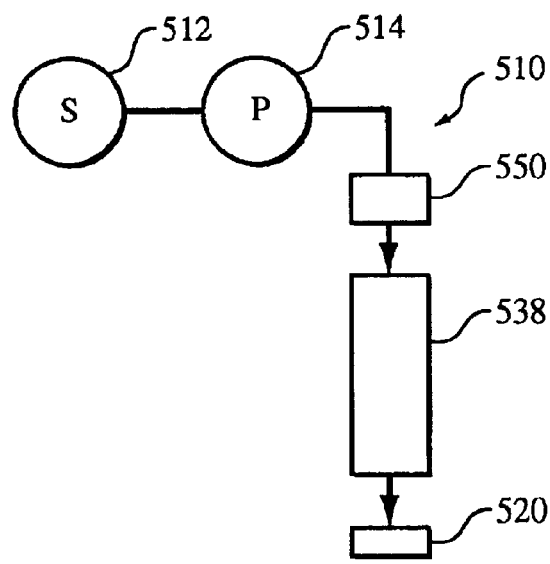
FIG. 20 is a schematic diagram of a chromatography system.

Referring to FIG. 20, there is shown chromatography system 510 which includes a source of solvent 512, pump 514, sample module 550, liquid chromatography composite column 538, and sample collection vessel 520. The composite column 538 is formed from two or more layers, as described above. In this system, the sample to be analyzed is preabsorbed onto media in sample module 550 prior to pumping solvent into module 550 and into composite column 538 to perform the separation procedure.

Figure 21:
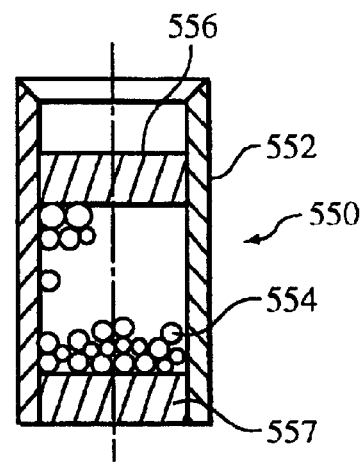
FIG. 21 is a longitudinal sectional view of a chromatography sample module used in the FIG. 20 system.

Referring to FIG. 21, it is seen that sample module 550 includes tube 552, porous plates 556, 557 (made of inert plastic porous frits), and chromatography media 554 (only partially shown in the figures) between porous plates 556, 557.

As appears from FIG. 24, sample module 550 is designed to fit within composite column 638 at the entrance thereof and to be sealably connected to the sealing head. The tube 552 is designed to fit within composite column 638 with minimal space between the two; in particular, there is 0.000" to 0.010" of radial clearance. The tube 552 can be a composite tube formed from two or more layers. An innermost layer can be formed from a chemically inert material, as described above in reference to embodiments of composite columns. A second layer, which can be the outermost layer or an intermediate layer, can be formed from a rigid and deformable material, also as described above in reference to composite columns.

Sample module 550 can be filled with media that is the same as or is different from the media of composite column 638. The sample is dissolved in the required solvent and added to the top of sample module 550, where it is drawn into the media by capillary action. This dissolution solvent is then removed by drying or evaporation. Sample module 550 may also be placed in a vacuum chamber to enhance the drying or evaporation. Heat may also be applied.

After sample module 550 has dried, it can be placed directly inside composite column 638 so that the lower porous plate 657 is an in intimate contact with the surface of the separation media or with a porous plate within the composite column on top of the separation media.

Alternatively, sample module 550 can be placed in a remote tube connected by a solvent line. Alternatively, the sample can be dissolved in a separation solvent (or a weaker solvent), and added to sample module 550 by any of the techniques described above. The wet module can then be loaded into the column or into a remote tube.

Examples of the types of complex samples where this technique has particularly advantageous use include synthetic organic reaction mixtures and natural product extracts, (e.g., from fermentation broths or plants). These samples often need to be dissolved in a solvent not compatible with the optimized separation solvent. Solvents are organized according to their "solvent strength," where hexanes have a value close to zero, and methanol has a value of 0.95. Optimized separation eluents often have a lower solvent strength; e.g., hexane:ethylacetate 1:1 has a solvent strength of 0.295. If the sample needs to be dissolved in a strong solvent such as methanol, there will be a solvent strength difference of 0.655 seen initially after loading the sample onto the column, and this will impair the separation of the sample. If the sample dissolved in methanol is instead preadsorbed to the media in the sample module and dried, the sample will not face this impairment during separation.

Figure 22:
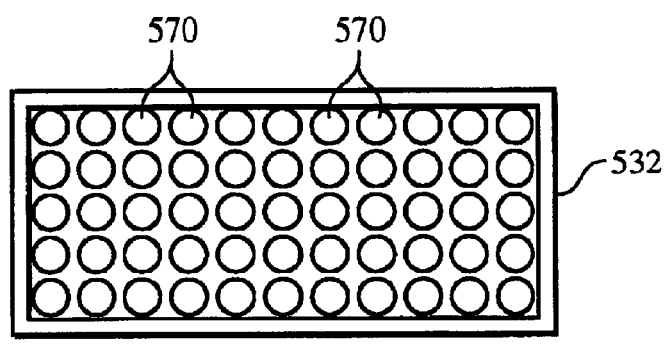
FIG. 22 is a plan view of a rack containing a plurality of the FIG. 21 sample modules in an array.
Figure 23:
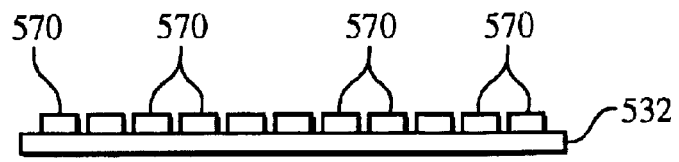
FIG. 23 is an elevation of the FIG. 22 rack and modules.

Referring to FIGS. 22 and 23, sample modules 550 can be supplied in racks 532, and a whole rack of sample modules 550 can be efficiently prepared at one time rather than one at a time.

Figure 24A:
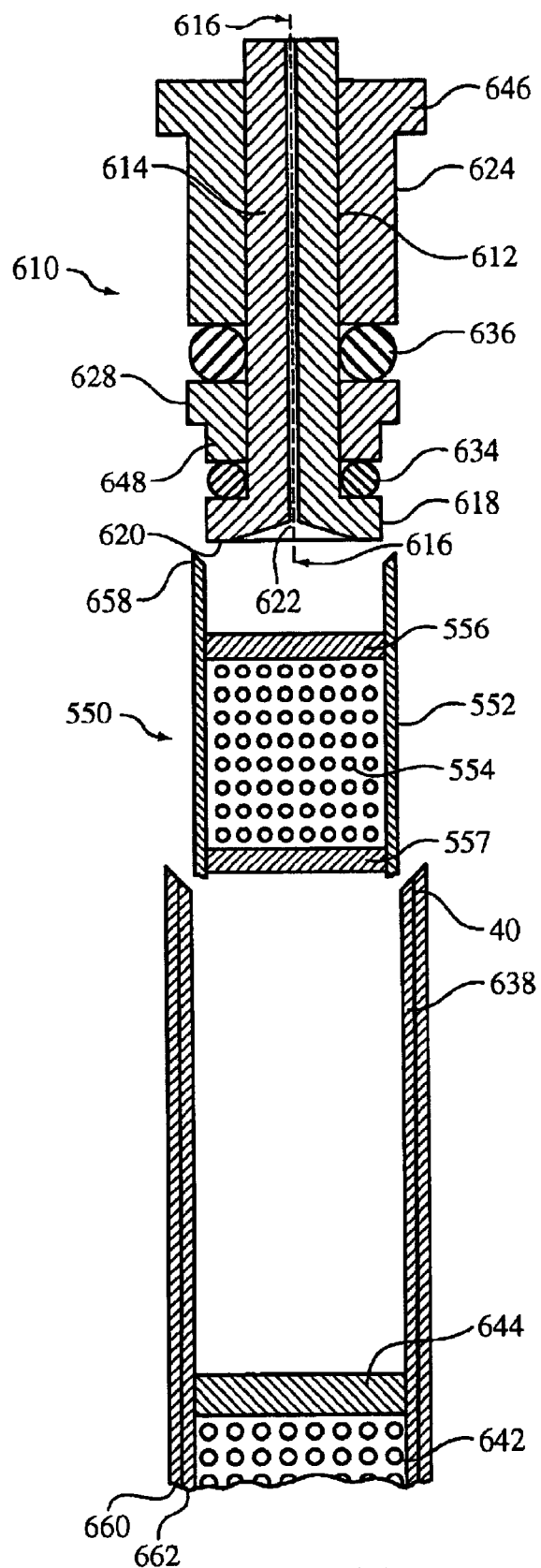
FIG. 24A shows an exploded longitudinal cross-sectional view of an alternate sealing apparatus with a sample module and chromatography column.

FIG. 24A shows the placement of a module 550 in a composite column 638 and the sealing of the module 550 and composite column 638 to a sealing head used to deliver solvent. Sealing head 610 has first head piece 612, second head piece 624, intermediate head piece 628, and first and second annular elastomeric sealing members 634, 636.

First head piece 612 has body 614 with longitudinal axis 616. First head piece 612 has outwardly extending shoulder 618, and contact face 620. Part of contact face 620 has a slightly conical shape or other concavity. First head piece 612 defines flow path 622 along axis 616.

Body 614 of first head piece 612 fits slidably through central openings in second head piece 624, intermediate head piece 628, and first and second elastomeric sealing members 634, 636.

Second head piece 624 has outwardly extending compression force receiving member 646. Intermediate head piece 628 has narrow portion 648 distal from second head piece 624.

First elastomeric sealing member 634 is adjacent to both shoulder 618 and narrow portion 648 of intermediate head piece 628. Second elastomeric sealing member 636 is adjacent to both intermediate head piece 628 and second head piece 624.

Sample module 550 has tube 552 that contains second chromatography media bed 554 bounded axially by second porous plates 556, 557. The outer diameter of tube 552 is sized so that sample module 550 fits into composite column 638. The inner diameter of tube 552 is sized so that it may slidably receive shoulder 618, first elastomeric sealing member 634, and narrow portion 648 of intermediate head piece 628.

Intermediate head piece 628, second elastomeric sealing member 636, and second head piece 624 are sized to fit slidably into composite column 638, having chamfered edges 640, filled with first chromatography media bed 642, which is bounded axially by first porous plates 644.

Figure 24B:
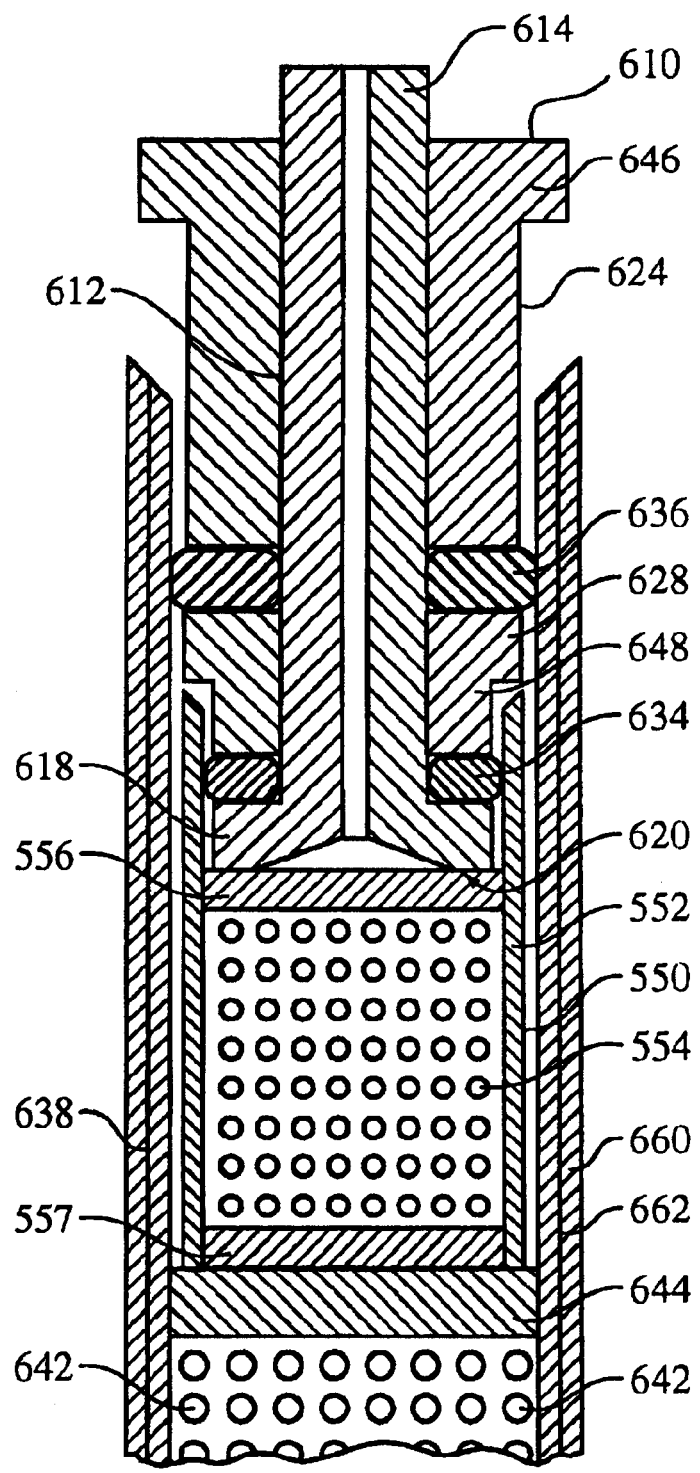
FIG. 24B shows a longitudinal cross-sectional view of an alternate sealing apparatus with a sample module and chromatography column.

Referring to FIG. 24B seals are formed with the apparatus by inserting sample module 550 into composite column 638 so that second porous plate 557 abuts first porous plate 644. Sealing head 610 is then inserted into composite column 638 and composite tube 552 of sample module 550, so that shoulder 618, first elastomeric sealing member 634, and narrow portion 648 are within tube 552, and contact face 620 abuts second porous plate 556. Sealing head 610 extends far enough into composite column 638 so that second elastomeric sealing member 636 opposes the inner surface of composite column 638.

Downward compressive force applied to outwardly extending compression force receiving member 646 causes second head piece 624 to slide relative to first head piece 612 and transmits compressive force to second elastomeric sealing member 636, intermediate head piece 628, first elastomeric sealing member 634, shoulder 618, second porous plate 556, first media bed 554, second porous plate 557, first porous plate 644, and first media bed 642. The compressive force causes first and second elastomeric sealing members 634, 636 to expand radially so that first elastomeric sealing member 634 forms a seal with tube 552 and second elastomeric sealing member 636 forms a seal with composite column 638.

The seals are released by applying an upward force to second head piece 624, thereby reducing the compressive force on the components of sealing head 610 and reducing the radial expansion of elastomeric sealing members 634, 636.

Composite column 638 is formed from an outer layer 660 and an inner layer 662. Preferably, the outer layer 660 is made of high-density polyethylene and the inner layer 662 is a chemically inert material, such as a fluoropolymer, for example PTFE, EFEP or materials sold under the trade names TEFLON and TEFZEL. Alternatively, the outer layer 660 can be made of polypropylene, stainless steel, aluminum, anodized aluminum, acetal, polycarbonate, glass or any other suitable material. The tube 552 is made of high-density polyethylene, but may be constructed of other materials, including glass or stainless steel. As discussed above, the tube 552 can be a composite tube formed of two or more layers, including an innermost layer formed from a chemically inert material, such as a fluoropolymer, for example, PTFE, EFEP, TEFLON and TEFZEL, and a second layer made of a rigid, deformable material, such as a high-density polyethylene, polypropylene, stainless steel, aluminum, anodized aluminum, acetal, polycarbonate, glass or the like. Preferably, elastomeric sealing member 522 is made of a fluorocarbon polymer, such as that sold under the trade name CHEMRAZ.

Composite chromatography columns and composite sample modules, like those described above, that employ an inner layer with a relatively low coefficient of friction (such as TEFLON) has the further advantage of enhancing the capacity of porous members to slide relative to the inner layer, thereby improving the axial compression of the media when such porous members are pressed against the media, for example, during the operation of sealing heads that press against the porous members.

The invention has been described in terms of particular embodiments. All of the columns discussed above can use the composite structure described herein. The composite columns may have 2, 3, 4, 5, 6 or any number of layers. Other embodiments are within the scope of the following claims.

What is claimed is:

1. A chromatography column comprising:

a tubular member having an inlet and outlet end, said tubular member including an innermost first layer comprising a substantially chemically inert material and a second layer;

first and second porous members disposed within said tubular member; and a chromatography or separation media disposed within said tubular member and bounded by said first and second porous members;

wherein said first porous member abuts said media and is spaced sufficiently from said inlet end to define a module receiving region for receiving a sample module entirely within said tubular member.

2. The chromatography column of claim 1, wherein said tubular member includes a plurality of layers, including at least the innermost first layer comprised of the chemically inert material and the second layer.

3. The chromatography column of claim 2, wherein the second layer is an intermediate layer and an outermost layer is comprised of the substantially chemically inert material.

4. The chromatography column of claim 2, wherein the substantially chemically inert material encapsulates said second layer, thereby forming an outermost layer comprised of the substantially chemically inert material.

5. The chromatography column of claim 1, wherein said tubular member further comprises a sealing region between said inlet end and said module receiving region, said sealing region being sufficiently long to receive a sealing head for making a seal with said innermost first surface of said tubular member.

6. The chromatography column of claim 1, wherein said tubular member further comprises a chamfered region near said inlet end.

7. The chromatography column of claim 1, wherein said second layer comprises polypropylene.

8. The chromatography column of claim 1, wherein said second layer comprises polyethylene.

9. The chromatography column of claim 1, wherein said second layer comprises stainless steel.

10. The chromatography column of claim 1, wherein said second layer comprises aluminum.

11. The chromatography column of claim 1, wherein said second layer comprises anodized aluminum.

12. The chromatography column of claim 1, wherein said second layer comprises acetal.

13. The chromatography column of claim 1, wherein said second layer comprises polycarbonate.

14. The chromatography column of claim 1, wherein said second layer comprises glass.

15. The chromatography column of claim 1, wherein said innermost first layer comprises a fluoropolymer.

16. The chromatography column of claim 15, wherein said fluoropolymer comprising polytetrafluoroethylene.

17. The chromatography column of claim 15, wherein said fluoropolymer is ethylene-fluorinated ethylene-propylene.

18. The chromatography column of claim 15, wherein said fluoropolymer is polytetrafluoroethylene.

19. The chromatography column of claim 15, wherein said fluoropolymer is ethylene-fluorinated ethylene-propylene.

20. The chromatography column of claim 1, wherein said second layer comprises polypropylene and said inner layer comprises polytetrafluoroethylene.

21. The chromatography column of claim 1, wherein said second layer comprises polyethylene and said inner layer comprises polytetrafluoroethylene.

* * * * *

UNITED STATES PATENT AND TRADEMARK OFFICE
CERTIFICATE OF CORRECTION

PATENT NO. : 6,783,673 B2  
DATED : August 31, 2004  
INVENTOR(S) : Jeffrey A. Horsman and Peter C. Van Davelaar It is certified that error appears in the above-identified patent and that said Letters Patent is hereby corrected as shown below:

Title page,
Item [56], References Cited, U.S. PATENT DOCUMENTS,
"2,998,036" reference, replace "Strashein" with -- Strasheim --; and
replace "3,574,352" with -- 3,574,252 --.

Column 10,
Line 21, replace "that", with -- than --.

Column 14,
Line 67, delete "an".

Column 16,
Lines 23 and 29, replace "clastomeric" with -- elastomeric --.

Column 17,
Line 12, after "and" and before "is" insert -- said first member is also in slidable contact with said innermost first layer of said tubular member and --.
Line 18, after "the" and before "chemically" insert -- substantially --.

Signed and Sealed this

Twenty-first Day of March, 2006

JON W. DUDAS  
*Director of the United States Patent and Trademark Office*